(12) United States Patent
Yang et al.

(10) Patent No.: US 9,465,025 B2
(45) Date of Patent: *Oct. 11, 2016

(54) STABLE NEURAL STEM CELL LINES

(75) Inventors: Renji Yang, Silver Spring, MD (US); Karl K. Johe, Potomac, MD (US)

(73) Assignee: Neuralstem, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/424,238

(22) Filed: Apr. 15, 2009

(65) Prior Publication Data

US 2009/0263901 A1    Oct. 22, 2009

Related U.S. Application Data

(63) Continuation of application No. 10/047,352, filed on Jan. 14, 2002, now Pat. No. 7,544,511, which is a continuation-in-part of application No. 09/053,414, filed on Apr. 1, 1998, now abandoned, and a continuation of application No. 09/398,897, filed on Sep. 20, 1999, now abandoned, which is a continuation of application No. 08/919,580, filed on May 7, 1997, now Pat. No. 6,040,180, and a continuation-in-part of application No. 08/719,450, filed on Sep. 25, 1996, now Pat. No. 5,753,506.

(60) Provisional application No. 60/018,206, filed on May 23, 1996, provisional application No. 60/101,354, filed on Sep. 22, 1998.

(51) Int. Cl.

| | |
|---|---|
| *C12N 5/22* | (2006.01) |
| *C12N 5/0797* | (2010.01) |
| *A61K 35/30* | (2015.01) |
| *G01N 33/50* | (2006.01) |
| *C12N 5/16* | (2006.01) |
| *C12N 5/0793* | (2010.01) |
| *G01N 33/94* | (2006.01) |
| *A61K 35/12* | (2015.01) |

(52) U.S. Cl.
CPC ........... *G01N 33/5058* (2013.01); *A61K 35/30* (2013.01); *C12N 5/0619* (2013.01); *C12N 5/0623* (2013.01); *C12N 5/16* (2013.01); *G01N 33/502* (2013.01); *G01N 33/5008* (2013.01); *G01N 33/5073* (2013.01); *G01N 33/9413* (2013.01); *A61K 35/12* (2013.01); *C12N 2500/25* (2013.01); *C12N 2500/90* (2013.01); *C12N 2501/11* (2013.01); *C12N 2501/115* (2013.01); *C12N 2501/13* (2013.01); *C12N 2501/148* (2013.01); *C12N 2501/392* (2013.01); *C12N 2501/395* (2013.01); *C12N 2501/91* (2013.01); *C12N 2506/02* (2013.01); *C12N 2510/00* (2013.01); *C12N 2510/02* (2013.01)

(58) Field of Classification Search
CPC .... C07N 5/0623; C07N 5/10; C12N 5/0623; C12N 5/16
See application file for complete search history.

(56) References Cited

U.S. PATENT DOCUMENTS

| | | |
|---|---|---|
| 4,753,635 A | 6/1988 | Sagen et al. |
| 4,980,174 A | 12/1990 | Sagen et al. |
| 5,082,670 A | 1/1992 | Gage |
| 5,166,065 A | 11/1992 | Williams et al. |
| 5,175,103 A | 12/1992 | Lee et al. |
| 5,411,883 A | 5/1995 | Boss et al. |
| 5,580,777 A | 12/1996 | Bernard et al. |
| 5,589,376 A | 12/1996 | Anderson et al. |
| 5,612,211 A | 3/1997 | Wilson et al. |
| 5,672,499 A | 9/1997 | Anderson et al. |
| 5,693,482 A | 12/1997 | Anderson et al. |
| 5,750,376 A | 5/1998 | Weiss et al. |
| 5,753,505 A | 5/1998 | Luskin |
| 5,753,506 A | 5/1998 | Johe |
| 5,770,414 A | 6/1998 | Gage et al. |
| 5,824,489 A | 10/1998 | Anderson et al. |
| 5,843,780 A | 12/1998 | Thomson |
| 5,849,553 A | 12/1998 | Anderson et al. |
| 5,851,832 A | 12/1998 | Weiss et al. |
| 5,928,947 A | 7/1999 | Anderson et al. |
| 5,932,473 A | 8/1999 | Swiderek et al. |
| 5,958,767 A | 9/1999 | Snyder et al. |
| 5,981,165 A | 11/1999 | Weiss et al. |
| 6,040,180 A | 3/2000 | Johe |
| 6,071,889 A | 6/2000 | Weiss et al. |
| 6,284,539 B1 | 9/2001 | Bowen et al. |

(Continued)

FOREIGN PATENT DOCUMENTS

| | | |
|---|---|---|
| EP | 0 233 838 | 8/1987 |
| JP | 2002-526065 | 8/2002 |

(Continued)

OTHER PUBLICATIONS

Xu, L. et al., "Glucocorticoid receptor and protein/RNA synthesis-dependent mechanisms underlie the control of synaptic plasticity by stress," PNAS, vol. 95, pp. 3204-3208, 1998.

(Continued)

*Primary Examiner* — Robert C Hayes
(74) *Attorney, Agent, or Firm* — Morgan, Lewis & Bockius LLP; Christopher J. Betti

(57) ABSTRACT

A systematic and efficient method for establishing stable neural stem cell lines and neuronal progenitor lines is described. The resulting cell lines provide robust, simple, and reproducible cultures of human and other mammalian neurons in commercially useful mass quantities while maintaining normal karyotypes and normal neuronal phenotypes.

19 Claims, 11 Drawing Sheets

(56) References Cited

U.S. PATENT DOCUMENTS

| | | |
|---|---|---|
| 6,294,346 B1 | 9/2001 | Weiss et al. |
| 6,399,369 B1 | 6/2002 | Weiss et al. |
| 6,497,872 B1 | 12/2002 | Weiss et al. |
| 6,531,464 B1 | 3/2003 | Szabo et al. |
| 6,699,871 B2 | 3/2004 | Edmondson et al. |
| 7,101,709 B2 | 9/2006 | Weiss et al. |
| 7,115,418 B2 | 10/2006 | Weiss et al. |
| 7,361,505 B1 | 4/2008 | Weiss et al. |
| 2002/0107273 A1 | 8/2002 | Nakao et al. |
| 2003/0059369 A1 | 3/2003 | Kung et al. |

FOREIGN PATENT DOCUMENTS

| | | |
|---|---|---|
| WO | 89/03872 | 5/1989 |
| WO | 90/06757 | 6/1990 |
| WO | 91/02003 | 2/1991 |
| WO | 91/09936 | 7/1991 |
| WO | 91/17242 | 11/1991 |
| WO | 93/01275 | 1/1993 |
| WO | 93/09802 | 5/1993 |
| WO | 94/02593 | 2/1994 |
| WO | 94/03199 | 2/1994 |
| WO | 94/04675 | 3/1994 |
| WO | 94/10292 | 5/1994 |
| WO | 95/13364 | 5/1995 |
| WO | 96/09543 | 3/1996 |
| WO | 96/15226 | 5/1996 |
| WO | 98/48001 | 10/1998 |
| WO | 99/01159 | 1/1999 |
| WO | 99/11758 | 3/1999 |
| WO | 00/17323 | 3/2000 |

OTHER PUBLICATIONS

Yamada et al., "NMDA receptor mediated Ca2+ responses in neurons differentiated from p53−/− immortalized Murin neural stem cells," (1999) Neurosci. Letters 264, pp. 165-167.

Yan J. et al., "Differentiation and Tropic/Trophic Effects of Exogenous Neural Precursors in the Adult Spinal Cord," vol. 480, pp. 101-114, 2004.

Yan, J. et al., "Grafted Human Neural Stem (NS) Cells Differentiate Into Neurons, Migrate Long Distance and Project Axons in Spinal Cord and the Roots of Adult Rats," Program No. 150.19, Abstract Viewer/Ininerary Planner. Society for Neuroscience, 2003.

Ye et al., "FGF and Shh Signals Control Dopaminergic and Serotonergic Cell Fate in the Anterior Neural Plate," Cell vol. 93:755-766 (1998).

Yoshimoto, Y. et al, "The Effect of Cool Storage on the Survivability of Intraventricular Rat Fetal Ventral Mesencephalic Graft," Duke Med Cent Lib 34.P 1, p. 208, 1991.

Zetterstrom et al., "Cellular expression of the immediate early transcription factors Nurr I and NGF1-B suggests a gene regulatory role in several brain regions including the nigrostriatal dopamine system," Molecular Brain Research, vol. 41, pp. 111-120, 1996.

Zetterström et al., "Dopamine Neuron Agenesis in Nurr1-Deficient Mice," Science 276:248-250 (1997).

Zhang, R. et al, "A nitric oxide donor induces neurogenesis and reduces functional deficits after stroke in rats," Ann. Neurol., vol. 50, pp. 602-611, 2001.

Falk, A., et al., "Amphiregulin is a mitogen for adult neural stem cells", Journal of Neuroscience Research, 69:757-762, (2002).

Feldman, D.H., et al., "Differentiation of Ionic Currents in CNS Progenitor Cells: Dependence upon Substrate Attachment and Epidermal Growth Factor," Experimental Neurology 140, 206-217 (1996).

Feron, F., et al., "Stress induces neurogenesis in non-neuronal cell cultures of adult olfactory epithelium", Neuroscience, 88:571-583, (1999).

Finger, S., et al., "Nimodipine and Neural Grafts", Duke Med. Cent. Lib., 34(1'2):208, (1991).

Finley, M. et al., "Synapse Formation and Establishment of Neuronal Polarity by P19 Embryonic Carcinoma and Embryonic Stem Cells," The Journal of Neurosciences, 16(3): 1056-1065 (1996).

Fischer, A.J., et al., "Exogenous Growth Factors Induce the Production of Ganglion Cells at the Retinal Margin", Development, 129:2283-2291, (2002).

Flax J.D., et al., "Engraftable human neural stem cells respond to developmental cues, replace neurons, and express foreign genes", Nature Biotechnology, 16:1033-1039, (1998).

Frappaz, D., et al., "Enhancement of Growth of Primary Metastatic Fresh Human Tumors of the Nervous system by Epidermal Growth Factor in Serum-free Short Term Culture", Neurosurgery, 23:355-359, (1988).

Frederiksen, K. et al., "Immortalization of Precursor Cells from the Mammalian CNS," Neuron, vol. 1, 439-448 (1988).

Fujiwara, Y., et al., "Intravenously Injected Neural Progenitor Cells of Transgenic Rats Can Migrate to the Injured Spinal Cord and Differentiate Into Neurons, Astrocytes and Oligodendrocytes", Neuroscience Letters, 366(3):287-291, (2004).

Gage, F.H., et al., "Isolation, Characterization, and use of Stem Cells From the CNS", Annu. Rev. Neurosci.,18:159-192, (1995).

Glasky, et al., "Update: Central and Peripheral Nervous Systems AIT-082, a novel purine derivative with neuroregenerative properties", Exp. Opin. Invest Drugs, 6:1413-1417, (1997).

Godfraind, C. et al., "In Vivo Analysis of Glial Cell Phenotypes during a Viral Demyelinating Disease in Mice," The Journal of Cell Biology, vol. 109, pp. 2405-2416 (1989).

Goldman, S.A., et al., "In vitro neurogenesis by neuronal precursor cells derived from the adult songbird brain", The Journal of Neuroscience, 12:2532-2541, (1992).

Gould, E., et al., "Inaugural Article: Adult-generated hippocampal and neocortical neurons in macaques have a transient existence", PNAS, 98:10910-10917, (2001).

Green, S., et al., "Human oestrogen receptor cDNA: sequence, expression and homology to v-erb-A", Nature, 320:134-139, (1986).

Gritti, A., et al., "Multipotential Stem Cells from the Adult Mouse Brain Proliferate and Self-Renew in Response to Basic Fibroblast Growth Factor", The Journal of Neuroscience, 16:1091-1100, (1996).

Gu W. et al., "Cortical neurogenesis in adult rats after reversible photothrombotic stroke", Journal of Cerebral Blood Flow and Metabolism, vol. 20, pp. 1166-1173, 2000.

Guentert-Lauber, B. et al., "Responsiveness of Astrocytes in Serum-Free AggregateCultures to Epidermal Growth Factor: Dependence on the Cell Cycle and the Epidermal Growth Factor Concentration," Dev. Neurosci. 7: 286-295 (1985).

Hall, et al., "An Introduction to Molecular Neurobiology", p. 357, 1992.

Hata, M., et al., "A decrease in the wet-dog shakes response to the second administration of kainic acid in juvenile rats", Biol. Abstr., 92(31832), (1991).

Hauser, K.F., et al., "Opioids intrinsically inhibit the genesis of mouse cerebellar granule neuron precursors in vitro: differential impact of mu and delta receptor activation on proliferation and neurite elongation", European Journal of Neuroscience, 12:1291-1293, (2000).

Hermanson, M., et al., "PDGF and its receptors following facial nerve axotomy in rats: expression in neurons and surrounding glia", Exp. Brain Res., 102:415-422, (1995).

Hollenberg et al., "Epidermal Growth Factor: Receptors in Human Fibroblasts and Modulation of Action by Cholera Toxin," Proc. Nat. Acad. Sci. USA, vol. 70, No. 10, pp. 2964-2968, Oct. 1973.

Honegger, P., et al., "Growth and Differentiation of Aggregating Fetal Brain Cells in a Serum-Free Defined Medium", Nature, 282:305-308, (1979).

Honkaniemi, J., et al., "Focal brain injury induces multiple immediate early genes encoding zinc finger transcription factors", Molecular Brain Research, 28:157-163, (1995).

Horcholle-Bossavit, G., et al., "Postnatal development of peroneal motoneurons in the kitten", Biol. Abstr., 90(78579), (1990).

(56) References Cited

OTHER PUBLICATIONS

Hoshimaru, M., et al., "Differentiation of the immortalized adult neuronal progenitor ce line HC2S2 into neurons by regulatable suppresision of the v-myc oncogene", Proc. Natl. Acad., 93:1518-1523, (1996).
Howland, et al., "Focal loss of the glutamate transporter EAAT2 in a transgenic rat model of SODI mutant-mediated amyotrophic lateral sclerosis (ALS)", PNAS, 99:1604-1609, (2002).
Hunter, S.F., et al., "Growth factor responses of enriched bipotential glial progenitors", Biol. Abstr., 90(78581), (1990).
Isacson, O., "The production and use of cells as therapeutic agents in neurodegenerative diseases," The Lancet Neurology, 2:417-424, (2003).
Ishibashi, et al., "Human Neural Stem/Progenitor Cells, Expanded in Long-Term Neurosphere Culture, Promote Functional Recovery After Focal Ischemia in Mongolian Gerbils", Journal of Neuroscience Research, 78:215-223, (2004).
Jain, M., et al., "GABAergic Immunoreactivity Is Predominant in Neurons Dervied From Expanded Human Neural Precursor Cells in Vitro", Experimental Neurology, 182(1):113-123, (2003).
Jelitai, M., et al., "Regulated appearance of NMDA Receptor Subunits and Channel Functions Duriing in Vitro Neuronal Differentiation", Journal of Neurobiology, 51:54-65, (2002).
Jin, K., et al., "Stem cell factor stimulates neurogenesis in vitro and in vivo", The Journal of Clinical Investigation, 110:311-319, (2002).
Jin, K., et al., "Vascular endothelial growth factor (VEGF) stimulates neurogenesis in vitro and in vivo", PNAS, 99:11946-11950, (2002).
Jones-Villeneuve, et al., "Retinoic Acid Induces Embryonal Carcinoma Cells to Differentiate into Neurons and Glial Cells", The Journal of Cell Biology, 94:253-262, (1982).
Jung, et al., "Novel pluripotential neural progenitor lines exhibiting rapid controlled differentiation to neurotransmitter receptor-expressing neurons and glia," Eur. J. Neuroscj., vol. 10 pp. 3246-3256 (1998).
Kehl, L.J., et al., "Neurogenesis in postnatal rat spinal cord: a study in primary culture", Science, 276:586-589, (1997).
Kempermann, G., et al., "Depressed new neurons-adult hippocampal neurogenesis and a cellular plasticity hypothesis of major depression", Biological Psychiatry, 54:499-503, (2003).
Kempermann, G., et al., "Genetic determinants of adult hippocampal neurogenesis correlate with acquisition, but not probe trial performance, in the water maze task", European Journal of Neuroscience, 16:129-136, (2002).
Kershaw, T.R., et al., "Foetal H-2Kb-tsA58 Transgenic Mouse Tissue Develops in a Similar Manner to ISO Geneic Foetal Tissue when Transplanted into Adult Mouse Brain", Duke Med. Cent. Lib., 34(4):208, (1991).
Kilpatrick, et al., "Cloning and Growth of Multipotential Neural Precursors: Requirements for Proliferation and Differentiation", 10:255-265, (1993).
Kilpatrick, T.J., Richards, L.J., and Bartlett, P.F., "The Regulation of Neural Precursor Cells within the Mammalian Brain," Mol. Cell. Neurosci., 6, 2-15, (1995).
Kilpatrick, T.J., and Bartlett, P.F., "Cloned Multipotential Precursors from the Mouse Cerebrum Require FGF-2, Whereas Glial Restricted Precursors Are Stimulated with Either FGF-2 or EGF," J. Neurosci., 15(5):3653-3661 (1995).
Kitani, H., et al., "Isolation and Characterization of Mouse Neural Precursor Cells in Primary Culture", In Vitro Cell. Dev. Biol., 27A:615-624, (1991).
Kuhn, H.G., et al., "Neurogenesis in the dentate gyrus of the adult rat: age-related decrease of neuronal progeneitor proliferation", The Journal of Neuroscience, 16:2027-2033, (1996).
Kumar, et al., "Localisation of the oestradiol-binding and putative DNA-binding domains of the human oestrogen receptor," The EMBO Journal, vol. 5, No. 9, pp. 2231-2236, (1986).
Law et al., "Identification of New Brain-Specific Transcription Factor, NURR 1," Molecular Endocrinology, pp. 2129-2135, 1992.

Ahmed, S. et al., "BDNF Enhances the Differentiation but Not the Survival of CNS Stem Cell-Derived Neuronal Precursors," The Journal of Neuroscience, 15(8): 5765-5778 (1995).
Almazan, et al., "Epidermal Growth and Bovine Growth Hormone Stimulate Differentiation and Myelination of Brain Cell Aggregates in Culture", Developmental Brain Research, 21:257-264, (1985).
Almazan, G., et al., "Triiodothyronine Stimulation of Oligodendroglial Differentiation and Myelination", Dev. Neurosci, 7:45-54, (1985).
Anchan, R.M., et al., "EFG and TGF-a Stimulate Retinal Neuroepithelial Cell Proliferation in Vitro", Neuron, 6:923-936, (1991).
Arsenijevic, Y., et al., "Isolation of multipotent neural precursors residing in the cortex of the adult human brain", Experimental Neurology, 170:48-62, (2001).
Avellana-Adalid, V., et al., "Expansion of Rat Oligodendrocyte Progenitors into Proliferative "Oligospheres" that Retain Differentiation Potential", Journal of neuroscience Research, 45:558-570, (1996). http://www3.interscience.wiley.com/cgi-bin/abstract/67559/ABSTRACT.
Baas, P.W. et al., "Polarity orientation of microtubules in hippocampal neurons: Uniformity in the axon and nonuniformity in the dendrite," Proc. Natl. Acad. Sci. USA, vol. 85, pp. 8335-8339 (1988).
Baetge, E.E., et al., "Neural Stem Cells for CNS Transplantation", Annals New York Academy of Sciences, 695:285-291, (1993).
Barlett P. F., "Regulation of Neural Precursor Differentiation in the Embryonic and Adult Forebrain," Clinical and Experimental Pharmacology and Physiology, vol. 22, p. 559-562, 1995.
Barlett, P.F., et al., "Immortalization of mouse neural precursor cells by the c-myc oncogene", Neurobiology, 85:3255-3259, (1988).
Behl, C., "Apoptosis and Alzheimer's disease", Journal of Neural transmission, 107:1325-1344, (2000).
Bernard, O., et al., "Role of the c-myc and the N-myc Proto-Oncogenes in the Immortalization of Neural Precursors", Journal of Neuroscience Research, 24:9-20, (1989).
Birren, S.J. et al., "A v-myc-Immortalized Sympathoadrenal Progenitor Cell Line in Which Neuronal Differentiation is Initiated by FGF but Not NGF", Neuron, 4:189-201, (1990).
Bredesen, D.E., et al., "Neural Transplantation Using Temperature-sensitive Immortalized Neural Cells: A Preliminary Report", Annals of Neurology, 27:205-207, (1990).
Bremner, J.D., et al., "Hippocampal volume reduction in major depression" Am. J. Psychiatry, 157:115-117, (2000).
Brezun, J., et al., "Depletion in serotonin decreases neurogenesis in the dentate gyrus and the subventricular zone of adult rats", Neuroscience, 89:999-1002, (1999).
Broe, M et al., "Relationship between DNA fragmentation, morphological changes and neuronal loss in Alzheimer's disease and dementia with Lewy bodies", Acta Neuropathol, 101:616-624, (2001).
Brüstle O., et al., "Neuronal progenitors as tools for cell replacement in the nervous system," Neurobiology 1996, 6:688-695.
Brüstle O., et al., "Embryonic Stem Cell-Derived Glial Precursors: A Source of Myelinating Transplants", Science, 285:754-756, (1999).
Calof, A.L., et al., "Analysis of neurogenesis in a mammalian neuroepithelium: proliferation and differentiation of an olfactory neuron precursor in vitro", Neuron, 3:115-127, (1989).
Cambray-Deakin, M.A., "The expression of excitatory amino acid binding sites during neuritogenesis in the developing rat cerebellum", Biol Abstr, 90:78583, (1990).
Cameron, H.A., et al., "Regulation of neurogenesis by growth factors and neurotransmitters", Journal of Neurobiology, 36:287-306, (1998).
Cao, Q., et al., "Stem Cell Repair of Central Nervous System Injury", Journal of Neuroscience Research, 68:501-510, (2002).
Carpenter, M.K., et al., "Generation and Transplantation of EGF-Responsive Neural Stem Cells Derived from GFAP-hNGF Transgenic Mice", Experimental Neurology, 148:187-204, (1997).
Carpenter, M.K., et al., "In Vitro Expansion of a Multipotent Population of Human Neural Progenitor Cells", Experimental Neurology, 158:265-278, (1999).

(56) References Cited

OTHER PUBLICATIONS

Carpenter reexamination U.S. Appl. No. 90/008,862 (reexamination of U.S. Pat. No. 6,103,530) entitled "Cultures of Human CNS Neural Stem Cells," filed Oct. 2, 2007.
Castillo, S.O., et al., "Dopamine Biosynthesis Is Selectively Abolished in Substantia NigraNentral Tegmental Area but Not in Hypothalamic Neurons in Mice with Targeted Disruption of the Nurr1 Gene", Molecular and Cellular Neuroscience, 11:36-46, (1998).
Castillo, S.O., et al., "Organization, Sequence, Chromosomal Localization, and Promoter Identification of the Mouse Orphan Nuclear Receptor Nurr1 Gene", Genomics, 41:250-257, (1997).
Cattaneo, E., et al., "Proliferation and differentiation of neuronal stem cells regulated by nerve growth factor", Letters to Nature, 347:762-765, (1990).
Cepko, C.L., "Immortalization of Neural Cells Via Retrovirus-Mediated Oncogene Transduction", Annu. Rev. Neurosci., 12:47-65, (1989).
Chabot, P., "Transient expression of an intermediate filament-associated protein (IFAPa-400) during in vivo and in vitro differentiation of chick embryonic cells derived form neuroectoderm", Biol Abstr, 90:78578, (1990).
Conover, J.C. et al., "Ciliary neurotrophic factor maintains the pluripotentiality of embryonic stem cells," Development 119, 559-565 (1993).
Coon, H.G., et al., "Cell cultures of neuroblasts from rat olfactory epithelium that show odorant responses", Neurobiology, 86:1703-1707, (1989).
Coppell, A.L., et al., "Bi-phasic change in BDNF gene expression following antidepressant drug treatment", Neuropharmcaology, 44:903-910, (2003).
Cummings, B.J., et al., "Human Neural Stem Cells Differentiate and Promote Locomotor Receovery in Spinal Cord-Injured Mice", Proceedings of the National Academy of Sciences of the United States of America, 102(39):14069-14074, (2005).
Czeh, B., et al., "Stress-induced changes in cerebral metabolites, hippocampal volume, and cell proliferation are prevented by antidepressant treatment with tianepine", PNAS, 98:12796-12801, (2001).
Davis, A., et al., "A self-renewing multipotential stem cell in embryonic rat cerebral cortex", Letters to Nature, 372:263-266, (1994).
DiCicco-Bloom, E., et al., "Neuroblast Mitosis in Dissociated Culture: Regulation and Relationship to Differentiation", The Journal of Cell Biology, 110:2073-2086, (1990).
Drago, J., et al., "A Method for the Isolation of Purified Murine Neuroepithelial Cells From the Developing Mouse Brain", Journal of Neuroscience Methods, 37:251-256, (1991).
Drago, J. et al.' "Basic Fibroblast Growth Factor Upregulates Steady-State Levels of Laminin B1 and B2 Chain mRNA in Cultured Neuroepithelial Cells", Experimental Cell Research, 196:246-254, (1991).
Drago, J., et al., "Fibroblast Growth Factor-Mediated Proliferation of Central Nervous System Precursors Depends on Endogenous Production of Insulin-like Growth Factor I", Neurobiology, 88:2199-2203, (1991).
Drago, J., et al., "Laminin through its Long Arm E8 Fragment Promotes the Proliferation and Differentiation of Murine Neuroepithelial Cells in Vitro", Experimental Cell Research, 192:256-265, (1991).
D'Sa, C. et al., "Antidepressants and neuroplasticity", Bipolar Disorders, 4:183-194, (2002).
Dutton, G.R., "Isolation, Culture, and Use of Viable Central nervous System Perikarya", Methods in Neuroscience, 2:87-102, (1990).
Ehrlich, M.E., et al., "DARPP-32 development in the caudate nucleus is independent of afferent input from the substantia nigra", Biol. Abstr. vol. 90(78582), (1990).
Eilers, M., et al., "Chimaeras of Myc oncoprotein and steroid receptors cause hormone-dependent transformation of cells", Letters to Nature, 340:66-68, (1989).

Eriksson, P.S., et al., "Neurogenesis in the adult human hippocampus", Nature Medicine, 4:1313-1317, (1998).
Escary, J. et al., "Leukaemia inhibitory factor is necessary for maintenance of haematopoietic stem cells and thymocyte stimulation," Nature, vol. 363, pp. 361-364 (1993).
Evans, R.M., "The Steroid and Thyroid Hormone Receptor Superfamily," Articles pp. 889-895 (1988).
Evrard, C. et al., "Immortalization of bipotential and plastic glio-neuronal precursor cells," Proc. Natl. Acad. Sci. USA, vol. 87, pp. 3062-3066 (1990).
Shou J. et al., "BMPs inhibit neurogenesis by a mechanism involving degradation of a transcription factor," Nature Neuroscience, vol. 2, pp. 339-345, 1999.
Sigma-Aldrich, Material Safety Data Sheet for Ethylenediaminetetraacetic Acid, for Complexometry, pp. 1-7 (1995).
Silani, V. et al., "Human Neuronal Cells in Culture: From Concepts to Basic Methodology," Boll. 1st. Sieroter. Mila., vol. 69, pp. 309-313, 1990.
Snyder et al., "Taking Stock and Planning for the Next Decade: Realistic Prospects for Stem Cell Therapies for the Nervous System," (2004) J. Neurosci. Res. 76:157-168.
Sorensen, K.A. et al., "Postembryonic neurogenesis in the Brain of Manduca Sexta," Society for Neuroscience Abstracts, vol. 16, p. 1147, 1990.
Sternfeld, M.D. et al., "Cultured Human Retinal Pigment Epithelial Cells Express Basic Fibroblast Growth Factor and its Receptor," Current Eye Research, vol. 8, pp. 1029-1037, 1989.
Stewart, J.S. et al., "Olfactory bulb and sensory epithelium in goldfish: Morphological alterations accompanying growth," Ref. No. 78577. Biol Abstr vol. 90, 1990.
Stone et al., "Definition of Regions in Human c-mycThat Are Involved in Transformation and Nuclear Localization," Molecular and Cellular Biology vol. 7, No. 5, pp. 1697-1709, 1987.
Svendsen, C.N. & Rosser, A.E., "Neurones from stem cells?" Trends in Neuroscience vol. 18, No. 11, pp. 465-466 (1995).
Svendsen, C.N., Fawcett, J.W., Bentlage, C. & Dunnett, S.B., "Increased survival of rat EGF-generated CNS precursor cells using B27 supplemented medium," Exp. Brain Res. 102: 407-414 (1995).
Svendsen, C.N. et al., "Survival and Differentiation of Rat and Human Epidermal Growth Factor-Responsive Precursor Cells Following Grafting into the Lesioned Adult Central Nervous System," Experimental Neurology 137, 376-388 (1996).
Svendsen, C.N. et al., "A new method for the rapid and long term growth of human neural prescursor cells," Journal of Neuroscience Methods 85 (1998) 141-152.
Takahashi J. et al., "Retinoic acid and neurotrophins collaborate to regulate neurogenesis in adult-derived neural stem cell cultures," J Neurobiol, vol. 38, pp. 65-81, 1999.
Takahashi, T. et al., "Cell cycle kinetics of the El4 murine cerebral ventricular zone: estimates based upon S-Phase labeling with BUdR," Society for Neuroscience Abstracts, vol. 16, p. 1147, 1990.
Takeichi, M. et al., "Roles of Magnesium and Calcium Ions in Cell-to-Substrate Adhesion," Experimental Cell Research 74 (1972) 51-60.
Taupin P, et al., "FGF-2-responsive neural stem cell proliferation requires CCg, a novel autocrine/paracrine cofactor," Neuron, vol. 28, pp. 385-397, 2000.
Taylor, M. et al., "Induction of Differentiation of Rat Retinal, Germinal, Neuroepithelial Cells by dbcAMP," Journal of Neurobiology, vol. 21, pp. 470-481, 1990.
Temple, S., "Division and Differentiation of Isolated CNS Blast Cells in Microculture," Nature, vol. 340, pp. 471-473-1989.
Temple, S. et al., "Vertebrateneural progenitor cells: subtypes and regulation," Neurobiology 1996, 6:11-17.
Tenot, M. et al., Epidermal Growth Factor Enhances the Expression of an Edogenous Lectin in Aggregating Fetal Brain Cell Cultures, Journal of Neurochemistry, vol. 53, pp. 1435-1441, 1989.
Torelli, S. et al., "Human Fetal Brain Cultures: A Model to Study Neural Proliferation, Differentiation and Immunocompetence," Adv. Exp. Med. Biol, vol. 296, pp. 121-134, 1991.

(56) References Cited

OTHER PUBLICATIONS

Torres, R.A. et al., "Alteration of Neuronal Regulation of Astrocytoma Proliferation by Insertional Mutagenesis," Society for Neuroscience Abstracts, vol. 16, p. 1147, 1990.
Turner M.R. et al., "Abnormal cortical excitability in sporadic but not homozygous D90A SOD I ALS," J Neurol Neurosurg Psychiatry, vol. 76, pp. 1279-1285, 2005.
Unsicker et al., "Growth factor function in the development and maintenance of midbrain dopaminergic neruons: concepts, facts and prospects for TGF-β," Ciba Found. Symp. 196, pp. 70-84 (1996).
Van Praag et al., "Running enhances neurogenesis, learning, and long-term potentiation in mice," PNAS, vol. 96, pp. 13427-13431, 1999.
Van Praag et al., "Running increases cell proliferation and neurogenesis in the adult mouse dentate gyrus," Nature Neuroscience, vol. 2, pp. 266-270, 1999.
Vescovi et al., "Isolation and Cloning of Multipotential Stem Cells from the Embryonic Human CNS and Establishment of Transplantable Human Neural Stem Cell Lines by Epigenetic Stimulation," (1999) Exp. Neurol. 156, 71-83.
Vescovi, A.L., Reynolds, B.A., Fraser, D.D., and Weiss, S., "bFGF Regulates the Proliferative Fate of Unipotent (Neuronal) and Bipotent (Neuronal/Astroglial) EGF-Generated CNS Progenitor Cells," Neuron vol. 11, pp. 951-966 (1993).
Vicario-Abejon, C., Johe, K, Hazel, T., Collazo, D. & McKay, R., "Functions of Basic Fibroblast Growth Factor and Neurotrophins in the Differentiation of Hippocampal Neurons," Neuron vol. 15, 105-114 (1995).
Villa, A. et al., "Intracellular calcium ion stores in chicken purkinje neurons; Differential distribution of the low-affinity-high capacity calcium binding protein, calsequestrin, of calcium ATPase and of the ER luminal protein," Bip. Ref. No. 31830, Biol Abstr vol. 92, 1991.
Von Frijtag, J. C. et al., "Chronic imipramine treatment partially reverses the !nog-term changes of hipocampal synaptic plasticity in socially stressed rats," Neuroscience Letters, vol. 309, pp. 153-156, 2001.
Von Visger, J.R. et al., "Differentiation and Maturation of Astrocytes Derived from Neuroepithelial Progenitor Cells in Culture," Experimental Neurology 128: 34-40, 1994.
Vu, E.T. et al., "Evidence for a Computational Distinction Between Proximal and Distal Neuronal Inhibition," Science, vol. 255, pp. 1710-1712, 1992.
Wagner et al, "Induction of a midbrain dopaminergic phenotype in Nurr1-overexpressing neural stem cells by type 1 astrocytes,"1999, Nat. Biotech., vol. 17:, pp. 653-659.
Wainer, B.H. et al., "In vitro cell cultures as model of the basal forebrain," Adv Exp Med Biol., vol. 295, pp. 415-437, 1991.
Wang et al., "A regulatory system for use in gene transfer," (1994) PNAS vol. 91, pp. 8180-8184.
Wang et al., "Induction of dopaminergic neurono phenotype in the midbrain by Sonic hedgehog protein," Nature Medicine, vol. 1, pp. 1184-1188, 1995.
Watanabe, R.T. et al., "Rod Photoreceptor development in vitro: intrinsic properties of proliferating neuroepithelial cells change as development proceeds in the rat retina," NeuralCulture, Abstract, 1990.
Watt et al., "Nucleotide sequence of cloned cDNA of human c-myc oncogene," Nature 303: 725-728, 1983.
Weiss et al., "Multipotent CNS Stem Cells Are Present in the Adult Mammalian Spinal Cord and Ventricular Neuroaxis," The Journal of Neuroscience, vol. 16, pp. 7599-7609, 1996.
Weiss et al. reexamination U.S. Appl. No. 90/008,580 (reexamination of U.S. Pat. No. 5,851,832) entitled "In Vitro Growth and Proliferation of Multipotent Neural Stem Cells and Their Progeny," filed Apr. 5, 2007.
Weiss et al. reexamination U.S. Appl. No. 90/008,367 (reexamination of U.S. Pat. No. 6,294,346) entitled "Use of Multipotent Neural Stem Cells and Their Progeny for the Screening of Drugs and Other Biological Agents," filed Dec. 7, 2006.
Weiss et al. reexamination U.S. Appl. No. 90/008,581 (reexamination of U.S. Pat. No. 6,497,872) entitled "Neural Transplantation Using Proliferated Multipotent Neural Stem Cells and Their Prodigy," filed Apr. 5, 2007.
Weiss et al. reexamination U.S. Appl. No. 90/008,366 (reexamination of U.S. Pat. No. 7,101,709) entitled "Methods of Screening Biological Agents," filed Dec. 7, 2006.
Weiss, S. et al., "Is there a neural stem cell in the mammalian forebrain?" TINS vol. 19, No. 9, 1996, pp. 387-393.
Weissman, I.L., "Translating Stem and Progenitor Cell Biology to the Clinic: Barriers and Opportunities," Science (2000) 287:1442-1446.
Wohl C A, et al., "Retinoic acid enhances neuronal proliferation and astroglial differentiation in cultures of CNS stem cell-derived precursors," J Neurobiol, vol. 37, pp. 281-290, 1998.
Wolswijk et al., "Identification of an adult-specific glial progenitor cell" Development, 105:387-400 (1989).
Xing et al., "Rat nurrl is prominently expressed in perirhinal cortex, and differentially induced in the hippocampal dentate gyrus by electroconvulsive vs. kindled seizures," Molecular Brain Research, vol. 47, pp. 251-261, 1997.
Xu et al., "The extremem C terminus of progesterone receptor contains a transcriptional repressor domain that functions through a putative corepressor," Proc. Natl. Acad. Sci., vol. 93, pp. 12195-12199, 1996.
Lee, et al., The v-myconcogeneOncogene, 18:2997-3003, (1999).
Lee, A.L., et al., "Stress and depression: possible links to neurons death in the hippocampus", Bipolar Disorders, 4:117-128, (2002).
Lee, J., et al., "Dietary restriction increases the number of newly generated neural cells, and induces BDNF expression, in the dentate gyrus of rats", Journal of Molecular Neuroscience, 15:99-108, (2001).
Lepore, A.C., et al., "Neural Precursor Cells Can Be Delivered Into the Injured Cervical Spinal Cord by Intrathecal Injection at the Lumbar Cord", Brain Research, 1045(1-2):206-216, (2005).
Lichtenwalner, R.J., et al., "Intracerebroventricular infusion of insulin-like growth factor-I ameliorates the age-related decline in hippocampal neurogenesis", Neuroscience, 107:603-613, (2001).
Lindvall, et al., "Stem cell therapy for human neurodegenerative disorders—how to make it work," Nature Med., 10:S42-S50, (2004).
Ling, et al., "Differentiation of Mesencephalic Progenitor Cells into Dopaminergic Neurons by Cytokines," Exp. Neurol., 149, 411-423, (1998).
Littlewood, T.D., et al., "A modified oestrogen receoptor ligan-binding domain as an improved switch for the regulation of heterologous proteins". Nucleic Acids Research. 1995, vol. 23, No. 10, pp. 1686-1690, see abstract.
Llado, J. et al., "Neural Stem Cells Protect Againist Glutamate-Induced Excitotoxicity and Promote Survival of Injured Motor Neurons Thrrough the Secretion of Neurotrophic Factors," Molecular and Cellular Neurosciences, 27(3):322-331, (2004).
Lois, et al., "Proliferating subventricular zone cells in the adult mammalian forebrain can differentiate into neurons and glia," Proc. Nat'l Acad. Sci., 90:2074-2077, (1993).
Lovejoy, D.A., et al., "Primary structure of two forms of gonadotropin-releasing hormone from brains of the American alligator", Biol. Abstr., 92(31827), (1991).
Lucassen, P.J., et al., "Hippocampal apoptosis in major depression is a minor event and absent from subareas at risk for glucocorticoid overexposure", American Journal of Pathology, 158:453-468, (2001).
Lyman, W.D., et al., "Human Fetal Central Nervous System Organotypic Cultures", Developmental Brain Research, 60:155-160, (1991).
Ma, W., et al., "Acetylcholine stimulates cortical precursor cell proliferation in vitro via muscarinic receptor activation and MAP kinase phosphorylation", European Journal of Neuroscience, 12:1227-1240, (2000).
Madsen, T.M., et al., "Increased neurogenesis in a model of electroconvulsive therapy", Biological Psychiatry, 47:1043-1049, (2000).

(56) References Cited

OTHER PUBLICATIONS

Malberg, J.E., et al., "Chronic antidepressant treatment increases neurogenesis in adult rat hippocampus", The Journal of Neuroscience, 20:9104-9110, (2000).
Marin, N., et al., "0.-amyloid-induced activation of caspase-3 in primary cultures of rat neurons", Mechanisms of Ageing and Development, 119:63-67, (2000).
Marsala, M., et al., "Spinal Implantation of hNT Neurons and Neuronal Precursors: Graft Survival and Functional Effects in Rats With Ischemic Spastic Paraplegia", European Journal of Neuroscience, 20(9):2401-2414, (2004).
Masters, B.A., "Insulin-like growth factor I (IFG-I) receptors and IGF-I action in oligodendrocytes from rat brains", Biol. Abstr. 92(31828), (1991).
Mattson, M.P., "Stem cells as therapeutics for neurodegenerative disorders?" Expert Rev. Neurotherapeutics, 267-273, (2001).
Mauerhoff, T. et al., "Differential Expression and Regulation of Major Histocompatibility Complex (MHC) Products in Neural and Glial Cells of the Human Fetal Brain", Journal of Neuroimmunology, 18:271-289, (1988).
Mayo, W., al., "Pregnenolone sulfate and aging of cognitive functions: behavioral, neurochemical, and morphological investigations", Hormones and Behavior, 40:215-217, (2001).
McCarthy, M., et al., "Infection of Human Neural Cell Aggregate Cultures with a Clinical Isolate of Cytomegalovirus", Journal of Neuropathology and Experimental Neurology, 50:441-450, (1991).
McKay, R., et al., "Mechanisms Regulating Cell number and Type in the Mammalian Central Nervous System", Cold Spring Harbor Symposia on Quantitative Biology, LV:291-301, (1990).
McKay, R., et al., "Stem Cells in the Developing and Adult Brain," (abs.) (1995).
McKay, R., et al., "Stem Cells in the Central Nervous System," Science, 276, pp. 66-71 (1997).
Mervaala, E., et al., "Quantitative MRI of the hippocampus and amygdala in severe depression", Psychological Medicine, 30:117-125, (2000).
Morrison, R.S., et al., "Trophic Stimulation of Cultured Neurons from Neonatal Rat Brain by Epidermal Growth Factor", Science, 238:72-75, (1987).
Morrison, S.J., et al., "Regulatory Mechanisms in Stem Cell Biology," Cell, vol. 88,287-298, Feb. 7, 1997.
Murphy, M., et al., "Fibroblast Growth Factor Stimulates the Proliferation and Differentiation of Neural Precursor Cells in Vitro", Journal of Neuroscience Research, 25:463-475, (1990).
Murrell, W., et al., "Neurogenesis in adult human," NeuroReport, 7:1189-1194, (1996).
Mytilineou, C., et al., "Epidermal Growth Factor-Induced Survival and Proliferation of Neuronal Precursor Cells from Embryonic Rat Mesencephalon", Neuroscience Letters, 135:62-66, (1992).
Nakafuku, et al., "Establishment and Characterization of a Multipotential Neural Cell Line That Can Conditionally Generate Neurons, Astrocytes, and Oligodendrocytes in Vitro", Journal of Neuroscience Research, 41:153-168, (1995).
Nakagawa, S., et al., "Regulation of neurogenesis in adult mouse hippocampus by cAMP and the cAMP reponse element-binding protein", The Journal of Neuroscience, 22:3673-3682, (2002).
Nestler, E.J., et al., "Neurobiology of Depression", Neuron, 34:13-25, (2002).
Nibuya, M., et al., "Chronic antidepressant administration increases the expression of cAMP response element binding protein (CREB) in rat hippocampus", The Journal of Neuroscience, 16:2365-2372, (1996).
Nielsen, F.C., et al., "Receptor Binding, Endocytosis, and Mitogenesis of Insulin-Like Growth Factors I and II in Fetal Rat Brain Neurons", Journal of Neurochemistry, 56:12-21, (1991).
Ohkura, et al., "Structure, mapping and expression of a human NOR-1 gene, the third member of the Nur77/NGFI-B family," Biochim. Biophys. Acta, 1308:205-214, (1996).

Oka, S., et al, "Autologous Transplantation of Expanded Neural Precursor Cells Into the Demyelinated Monkey Spinal Cord", Brain Research, 1030(1):94-102, (2004).
Okabe, et al., "cDNA Cloning of a NGFI-B/nur77-Related Transcription Factor from an Apoptotic Human T Cell Line," J. Immunol., 154:3871-3879, (1995).
Okano, et al., "Neural stem cells and regeneration of injured spinal cord", Kidney International, 68:1927-1931, (2005).
Okano, H., "Neural stem cells: progression of basic research and perspective for clinical application," Keio Journal of Medicine, vol. 51, pp. 115-128, 2002.
Palmer T D. et al., "The Adult Rat Hippocampus Contains Primordial Neural Stem Cells," Molecular and Cellular Neuroscience 8, 389-404 (1997).
Palmer T D. et al., "Fibroblast growth factor-2 activates a latent neurogenic program in neural stem cells from diverse regions of the adult CNS," The Journal of Neuroscience, vol. 19, pp. 8487-8497, 1999.
Park K. et al., "Global gene and cell replacement strategies via stem cells," Gene Therapy, vol. 9, pp. 613-624, 2002.
Pena de Ortiz et al., "HZF-3, an immediate-early orphan receptor homologous to NURR1/NOT: Induction upon membrane depolarization and seizures," Mol. Brain Res. 38:1-13 (1996).
Perrone-Capano et al., "Epigenetic factors and midbrain dopaminergic neurone development," Bioessays vol. 18 No. 10 pp. 817-824 (1996).
Peterson D. A. et al., "Trophic factor therapy for neuronal death," Alzheimer Disease, 2nd Edition, Chapter 25, pp. 373-388, 1999.
Pham, K. et al., "Repeated restraint stress suppresses neurogenesis and induces biphasic PSA-NCAM expression in the adult dentate gyrus," European Journal of Neuroscience, vol. 17, pp. 879-886, 2003.
Piescinski, P. et al., "Neurogenesis of the amygdaloid complex in the rhesus monkey," Society for Neuroscience Abstracts, vol. 16, p. 1147, 1990.
Pincus D W. et al., "In vitro neurogenesis by adult human epileptic temporal neocortex," Clinical Neurosurgery, Chapter 2, pp. 17-25.
Pollerberg et al., "Generation of Cell Lines From Embryonic Quail Retina Capable of Mature Neuronal Differentiation," Journal of Neuroscience Research, vol. 41, pp. 427-442, 1995.
Pucilowski, O. et al., "Decreased hyperthermic effect of MK801 in selectively bred hypercholinergic rats," Ref. No. 31825. Biol Abstr vol. 92, 1991.
Puliam, L. et al., "A Normal Human Brain Cell Aggregate Model for Neurobiological Studies," Journal of Neuroscience Research, vol. 21, pp. 521-230, 1988.
Qu, T. et al., "Human neural stem cells improve cognitive function of aged brain," NeuroReport, vol. 12, pp. 1127-1132, 2001.
Raina, A K. et al., "Abortive apoptosis in Alzheimer's disease," Acta Neuropathol, vol. 101, pp. 305-310, 2001.
Rajan et al., "Neural Stem Cells and Their Munipulation," (2006) Methods in Ezymol. 419:23-52.
Rakic, P. "Radial Versus Tangential Migration of Neuronal Clones in the Developing Cerebral Cortex," Proc. Natl. Acad. Sci, USA, vol. 92, pp. 11323-11327, Dec. 1995.
Rao et el., "Immortalization and Controlled in Vitro Differentiation of Murine Multipotent Neural Crest Stem Cells," (1997) J. Neurobiol. 32, 722.
Rathbone M P. et al., "Trophic effects of purines in neurons and glial cells," Progress in Neurobiology, vol. 59, pp. 663-690, 1999.
Ray, J. and Gage, F.H., "Spinal Cord Neuroblasts Proliferate in Response to Basic Fibroblast Growth Factor," J. Neurosci. 14(6): 3548-3564 (1994).
Ray, J. Peterson, D., Schinstine, M. & Gage, F., "Proliferation, differentiation, and long-term culture of primary hippocampal neurons," Proc. Natl. Acad. Sci. USA vol. 90, pp. 3602-3606 (1993).
Reichmann et al., "Activation of an Inducible c-FosER Fusion Protein Causes Loss of Epithelial Polarity and Triggers Epithelial-Fibroblastoid Cell Conversion," (1992) Cell vol. 71, pp. 1103-1116.
Renoncourt et al., Neurons derived in vitro from ES cells express homeoproteins characteristic of motoneurons and interneurons (1998) Mechanisms of Development 79 pp. 185-197.

(56) References Cited

OTHER PUBLICATIONS

Rettig, W.J. et al., "Cell Type-specific Control of Human Neuronc-ctin Secretion by Polypeptide mediators and Phorbol Ester," The Journal of Histochemistry and Cytochemistry, vol. 37, pp. 1777-1786, 1989.
Rettig, W.J. et al., "Stimulation of Human Neuronectin Secretion by Brain-Derived Growth Factors," Brain Research, vol. 487, pp. 171-177, 1989.
Reynolds, B.A. et al., "A Multipotent EFG-Responsive Striatal Embryonic Progenitor Cell Produces Neuron and Astrocytes," The Journal of Neuroscience, vol. 12, pp. 4565-4574, 1992.
Reynolds, B.A. et al., "A Non-Transformed, Growth Factor Dependent Stem Cell Line Derived From the Embryonic Mouse CNS Produces Neurons, Astrocytes and Oligodendrocytes," Duke Med Cent Lib 34.P3, p. 208, 1991.
Reynolds, B.A. et al., "EGF- and TFCce-responsive striatal embryonic progenitor cells produce both neurons and astocytes," Society for Neuroscience Abstracts, vol. 16, p. 1147, 1990.
Reynolds, B.A. et al., "Generation of Neurons and Astocytes from Isolated Cells of the Adult Mammalian Central Nervous System," Science, vol. 255, pp. 1707-1709, 1992.
Righi et al., myc-Immortalized Microglial Cells Express a Functional Platelet-Activating Factor Receptor (1995) J. Neurochem. 64, 121-129.
Rind H. et al., "Synaptic Targeting of Retrogradely Transported Trophic Factors in Mononeurons: Comparison of Glial Cell Line-Derived Neurotrophic Factor, Brain-Derived Neurotrophic Factor, and Cardiotrophin-1 with Tetanus Toxin," The Journal of Neuroscience, vol. 25, pp. 539-549, 2005.
Romand, R. et al., "Development of tonotopy oin the inferior colliculus: 1. Electrophysiological mapping in house mice," Ref. No. 78580 Biol Abstr vol. 90, 1990.
Roth, K. A., "Caspases, apoptosis, and Alzheimer disease: causation, correlation, and confusion," Journal of Neuropathology and Experimental Neurology, vol. 60, pp. 829-838, 2001.
Rothstein J.D. et al., "Decreased Glutamate Transport by the Brain and Spinal Cord in Amyotrophic Lateral Sclerosis," The New England Journal of Medicine, vol. 326, pp. 1464-1468, 1992.
Roy N S, et al., "In vitro neurogenesis by progenitor cells isolated from the adult human hippocampus," Nature Medicine, vol. 6, pp. 271-277, 2000.
Rozental R. et al., "Differentiation of hippocampal progenitor cells in vitro: temporal expression of intercellular coupling and voltage- and ligand-gated responses," Developmental Biology, vol. 167, pp. 350-362, 1995.
Rutka, J.T. et al., "Characterization of Fetal Human Brain Cultures," Dev. Neurosci., vol. 9, pp. 154-173, 1987.
Ryder et al., "Establishment and Characterization of Multipotent Neural Cell Lines Using Retrovirus Vector-Mediated Oncogene Transfer," (1990) J. Neurobiol vol. 21, No. 2, pp. 356-375.
Sabate, O., Horellou, P., Vigne, E., Colin, P., Perricaudet, M., Buc-Caron, M.-H. & Mallet, J., Nature Genetics 9, 256-260 (1995).
Sah et al., Bipotent progenitor cell lines from the human CNS (1997) Nature Biotech. vol. 15, pp. 574-580.
Sales, N. et al., "Neutral endopeptidase 24.11 in rat peripheral tissues: comparative localization "ex vivo" and in vitroautoradiography," Ref. No. 31829 Biol Abstr vol. 92, 1991.
Saneto, R.P. et al., "Insulin/Insulin-Like Growth Factor I and Other Epigenetic Modulators of Myelin Basic Protein Expression in Isolated Oligodendrocyte Progenitor Cells," Journal of Neuroscience Research, Vo. 21, pp. 210-219, 1988.
Santarelli, L. et al., "Requirement of hippocampal neurogenesis for the behavioral effects of antidepressants," Science, vol. 301, pp. 805-809, 2003.
Sato, H. et al., "Somatostatin receptors in the senescent rat brain: A quantitative autoradiographic study," Ref. No. 31826, Biol Abstr vol. 92, 1991.
Satoh M. et al., "Promotion of neurogenesis in mouse olfactory neuronal progenitor cells by leukemia inhibitory factor in vitro," Neuroscience Letters, vol. 225, pp. 165-168, 1997.
Saucedo-Cardenas et al., "Cloning and structural organization of the gene encoding the murine nuclear receptor transcription factor, NURR1," Gene 187:135-139 (1997).
Saucedo-Cardenas et al., "Nurr1 is essential for the induction of the dopaminergic phenotype and the survival of ventral mesencephalic late dopaminergic precursor neurons," Proc. Natl. Acad. Sci. USA 95:4013-4018 (1998).
Scearce et al., "RNR-1, a Nuclear Receptor in the NGFI-B/Nur77 Family That Is Rapidly Induced in Regenerating Liver," J. Biol. Chem. vol. 268, No. 12, pp. 8855-8861 (1993).
Schapira, A., "Pathogenesis of Parkinson's disease," Bailliere's Clin. Neurol. vol. 6, No. 1, pp. 15-36 (1997).
Schinstine, M. et al., "Expression of Neuronal Antigens by Astrocytes Derived from EGF-Generated Neuroprogenitor Cells," Experimental Neurology 141, 67-78 (1996).
Schlaggar, B.L. et al., "Potential of Visual Cortex to Develop an Array of Functional Units Unique to Somatosensory Cortex," Science, vol. 252, pp. 1556-1560 (1991).
Scott B W. et al., "Neurogenesis in the dentate gyrus of the rat following electroconvulsive shock seizures," Experimental Neurology, vol. 165, pp. 231-236, 2000.
Seaberg R M. et al., "Adult rodent neurogenic regions: the ventricular subependyma contains neural stem cells, but the dentate gyrus contains restricted progenitors," The Journal of Neuroscience, vol. 22, pp. 1784-1793, 2002.
Seigel, G.M. et al., "Differentiation of oncogenically altered chick neuroretinal cells by succinylated concanavalin A," Society for Neuroscience Abstracts, vol. 16, p. 1147, 1990.
Selvakumarun et al., "Myeloblastic Leukemia Cells Conditionally Blocked by Myc-Estrogen Receptor Chimeric transgenes for Terminal Differentiation Coupled to Growth Arrest and Apoptosis," (1993) Blood vol. 81, No. 9, pp. 2257-2262.
Shingo T. et al., "Erythropoietin regulates the in vitro and in vivo production of neuronal progenitors by mammalian forebrain neural stem cells," The Journal of Neuroscience, vol. 21, pp. 9733-9743, 2001.
Shirayama, Y. et al., "Brain-derived neurotrophic factor produces antidepressant effects in behavioral models of depression," The Journal of Neuroscience, vol. 22, pp. 3251-3261, 2002.
Shors T J. et al., "Neurogenesis in the adult is involved in the formation of trace memories," Nature, vol. 410, pp. 372-376, 2001.
Bjerkvig et al., "Reaggregation of Fetal Rat Brain Cells in a Stationary Culture System I: Methodology and Cell Identification," In Vitro Cellular & Development Biology, 22:4 180-192 (1986).
Dahlstrand et al., "Nestin mRNA expression correlates with the central nervous system progenitor cell state in many, but not all, regions of developing central nervous system," Developmental Brain Research 84:109-129 (1995).
Doering et al., "Isolation and identification of neuroblast precursor cells from mouse neopallium," Developmental Brain Research 5:229-233 (1982).
Eccleston et al., "Requirements for Brain Cell Attachment, Survival and Growth in Serum-Free Medium: Effects of Extracellular Matrix, Epidermal Growth Factor and Fibroblast Growth Factor" Dev. Neurosci 7:308-322 (1985).
Engebraaten et al., "Effects of EGF, bFGF, NGF and PDGF(bb) on cell proliferative, migratory and invasive capacities of human brain-tumor biopsies in vitro," Int. J. Cancer, 53:209-214 (1993).
Gage, F.H. et al., "Survival and differentiation of adult neuronal progenitor cells transplanted to the adult brain," Proc. Natl. Acad. Sci., vol. 92, pp. 11879-11883, Dec. 1995.
Hockfield et al., "Identification of Major Cell Classes in the Developing Mammalian Nervous System," The Journal of Neuroscience 5:12 3310-3328 (1985).
Johe, K. et al., "Single factors direct the differentiation of stem cells from the fetal and adult central nervous system," Genes & Development, vol. 10, pp. 3129-3140, 1996.
Law, et al., "Molecular Cloning of a Novel Member of theNuclear Receptor Superfamily Realted to the Orphan Receptor, TR2," Gene Expr., vol. 4, pp. 77-84, (1994).
Lendahl et al., "CNS Stem Cells Express a New Class of Intermediate Filament Protein," Cell 60:585-595 (1990).

(56) References Cited

OTHER PUBLICATIONS

Lumsden, A. et al., "Patterning the Vertibrate Neuraxis," Science, vol. 274, pp. 1109-1115, Nov. 15, 1996.
Mages, H. et al., "NOT, a Human Immediate-Early Response Gene Closely Related to the Steroid/Thyroid Hormone Receptor NAK1/TR3," Molecular Endocrinology, p. 1583-1591, 1994.
Monnet-Tschudi, F. et al. "Influence of Epidermal Growth Factor on the Maturation of Fetal Rat Brain Cells in Aggregate Culture," Dev Neurosci 1989, vol. 11, pp. 30-40.
Morshead et al., "Postmitotic Death Is the Fate of Constitutively Proliferating Cells in the Subependymal Layer of the Adult Mouse Brain," The Journal of Neuroscience 12(1):249-256 (1992).
Morshead et al., "Neural Stem Cells in the Adult Mammalian Forebrain: A Relatively Quiescent Subpopulation of Subependymal Cells," Neuron 13:1071-1082 (1994).
Price, "Brain Stems," Current Biology 5:3 232-234 (1995).
Qian, X et al., "FGF2 Concentration Regulates the Generation of Neurons and Glia from Multipotent Cortical Stem Cells," Neuron, vol. 18, pp. 81-93, Jan. 1997.
Redies et al., "Differentiation and Heterogeneity in T-Antigen Immortalized Precursor Cell Lines From Mouse Cerebellum," Journal of Neuroscience Research 30:601-615 (1991).
Resnick, J et al., "Long-term proliferation of mouse primordial germ cells in culture," Nature, vol. 359, pp. 550-551, Oct. 8, 1992.
Rudland, P.S. et al., "Growth Control in cultured Mouse Fibroblasts: Induction of the Pleiotypic and Mitogenic Responses by a Purified Growth Factor," Proc. Nat. Acad. Sci., vol. 71, No. 7, pp. 2600-2604, Jul. 1974.
Tohyama et al., "Nestin Expression in Embryonic Human Neuroepithelium and in Human Neuroepithelial Tumor Cells," Laboratory Investigation 66:3 303-313 (1992).
Trenkner et al., "Cell Reaggregation and Migration, Fiber and Synapse Formation," The Journal of Cell Biology 75:915-940 (1977).
Zeller et al., "The Timely Expression of Myelin Basic Protein Gene in Cultured Rat Brain Oligodendrocytes is Independent of Continuous Neuronal Influences," The Journal of Neuroscience 5:11 2955-2962 (1985).
Martz et al., "The Role of Cell-Cell Contact in "Contact" Inhibition of Cell Division: A Review and New Evidence," J. Cell Physiol., 79:189-210, (1971).
Reynolds, B.A. et al., "Clonal and Population Analyses Demonstrate That an EGF Responsive Mammalian Embryonic CNS Precursor Is a Stem Cell," Developmental Biology 175, 1-13 (1996).
Tropepe, V. et al., "Direct Neural Fate Specification from Embryonic Stem Cells: A Primitive Mammalian Neural Stem Cell Stage Acquired through a Default Mechanism," Neuron, vol. 30, 65-78, Apr. 2001.
Gritti, A. et al., "Multipotential Stem Cells from the Adult Mouse Brain Proliferate and Self-Renew in Response to Basic Fibroblast Growth Factor," The Journal of Neuroscience, vol. 16, pp. 1091-1100, 1996.
Sah et al., "Bipotent progenitor cell lines from the human CNS," (1997) Nature Biotech. 15:574.
Bartlett et al. Immortalization of mouse neural precursor cells by c-myc oncogene. Proc. Natl. Acad. Sci. USA vol. 85 3255-3259 May 1988 Neurobiology.
Rappa G. et al. Efficient expansion and gene transduction of mouse neural stem/progenitor fibronectin cells on recombinant, vol. 124, No. 4, Jan. 1, 2004, pp. 823-830.
University of Maryland Tissue Bank Summary, [retrieved from the Internet on Jun. 24, 2010], <http://medschool.som.umaryland.edu/btbank/NICHD-BTB-AboutUs.asp>.
University of Maryland Tissue Bank Catalog, printed Apr. 2010.
European Office Action for European Application No. 99 948 396.9, dated Aug. 27, 2013.

FIG. 3A
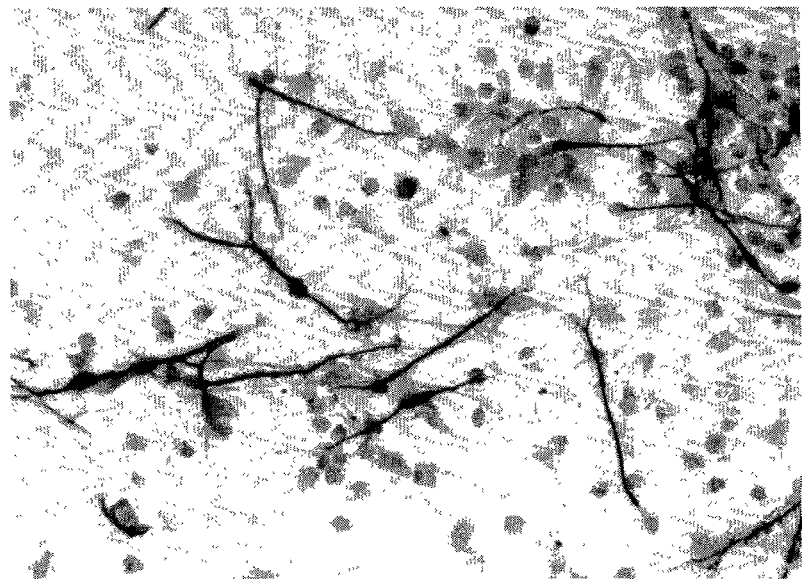
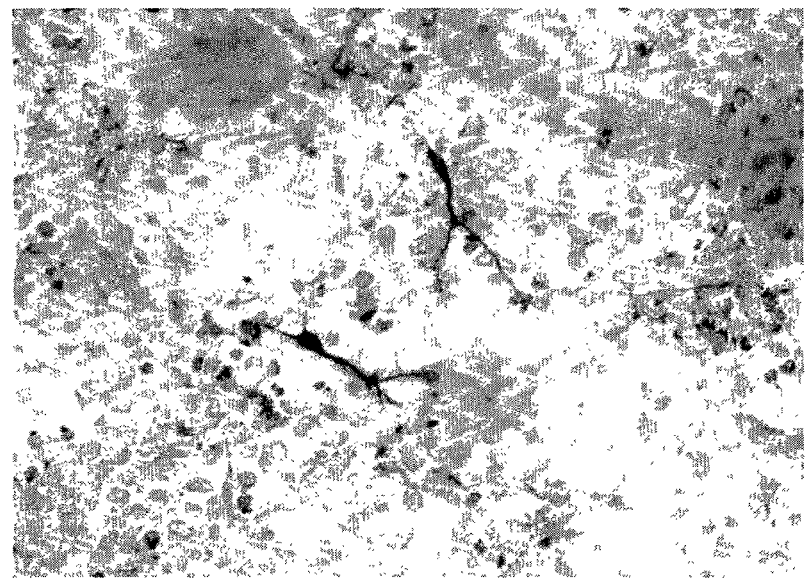
FIG. 3B

FIG. 3C
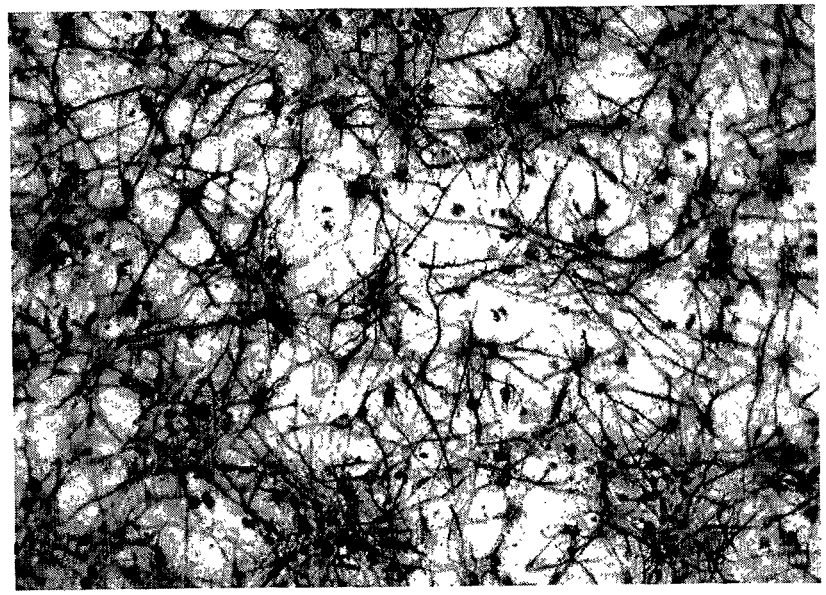
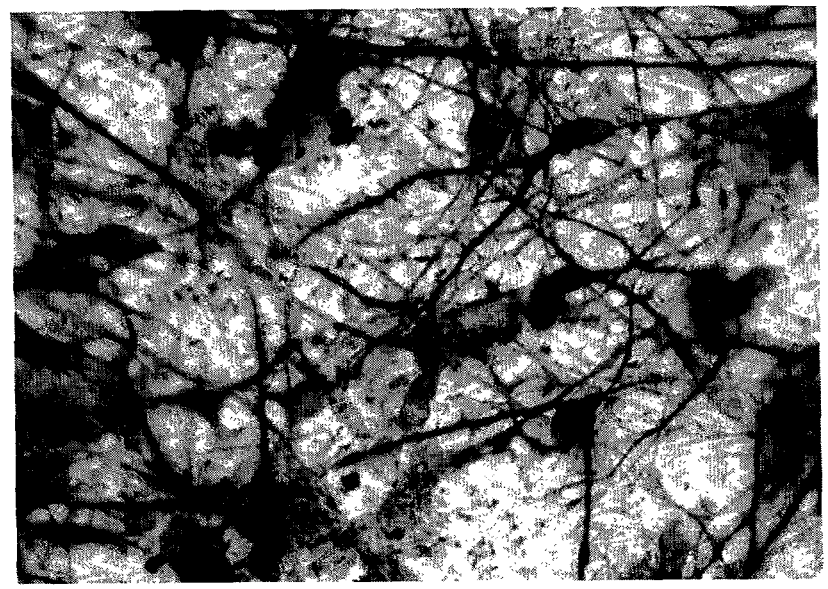
FIG. 3D

FIG. 3E
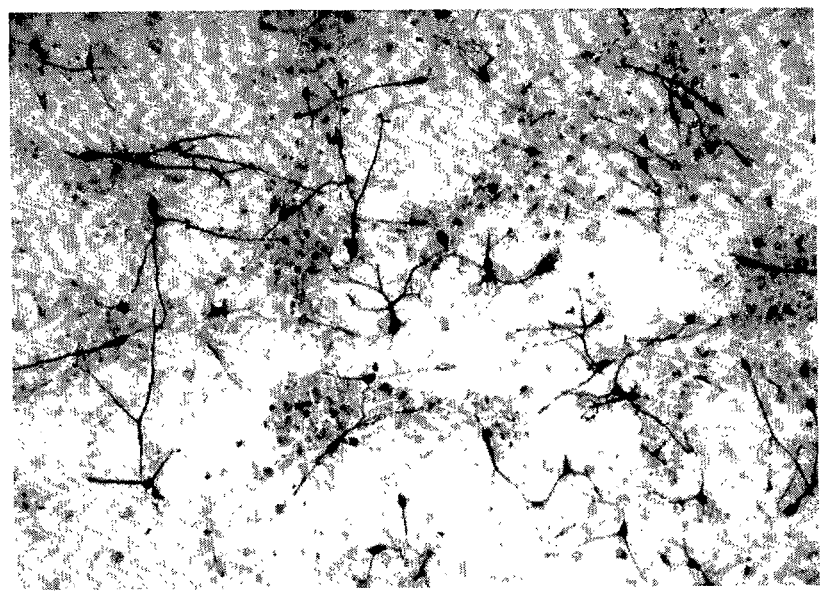
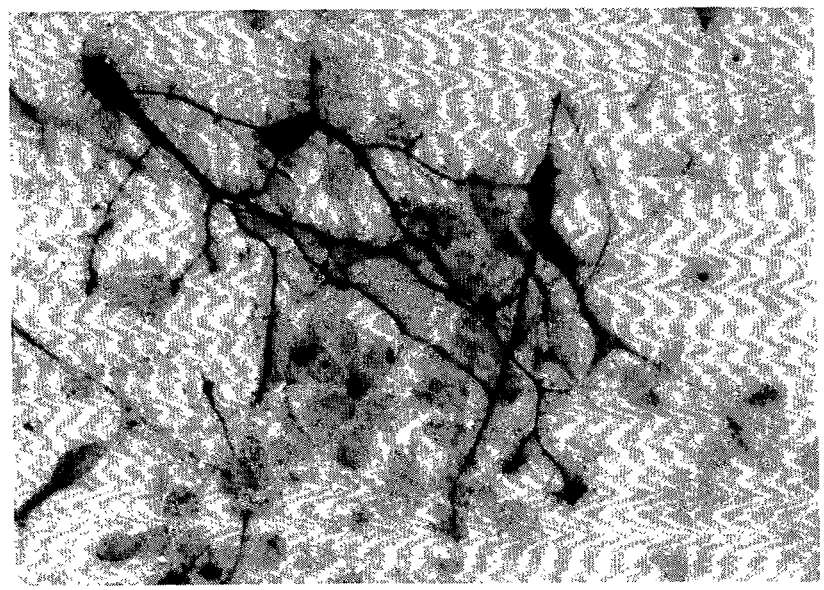
FIG. 3F

FIG. 3G
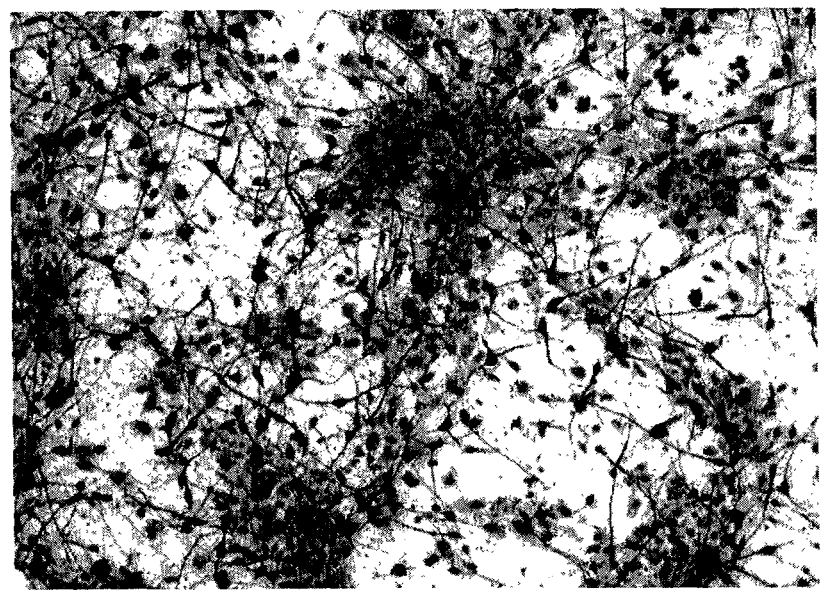
FIG. 3H

FIG. 3I
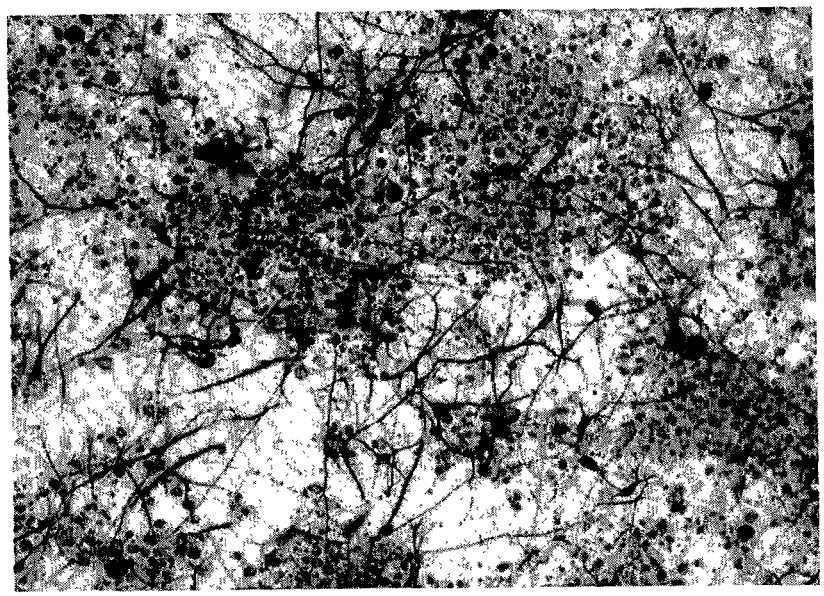
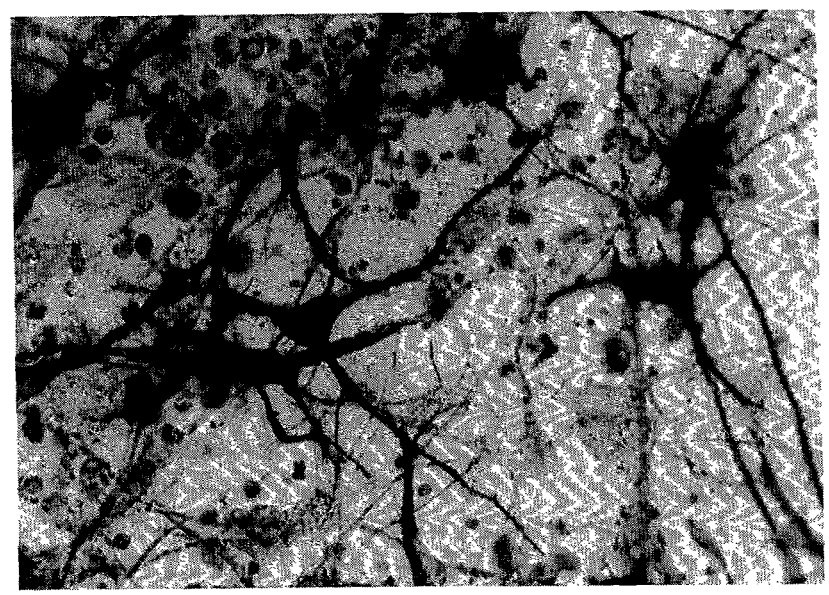
FIG. 3J

FIG. 3K
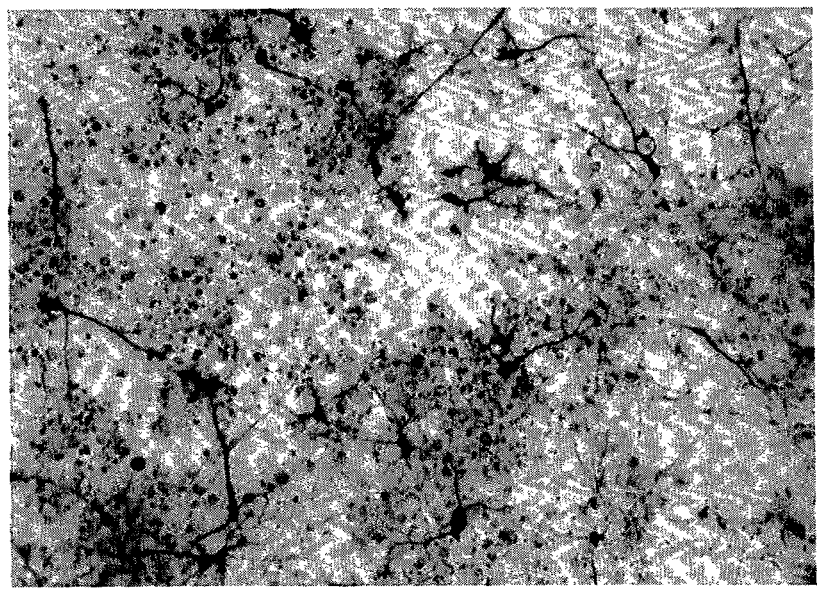
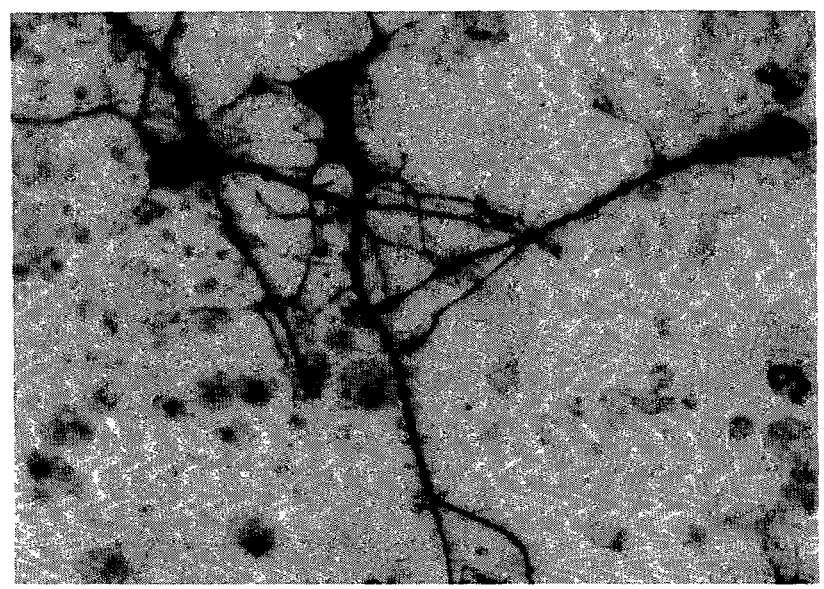
FIG. 3L

FIG. 5A
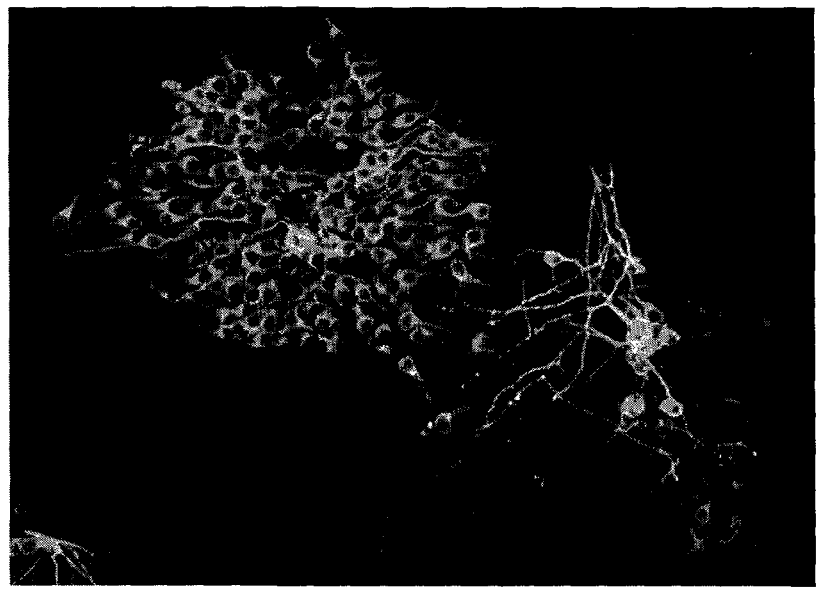
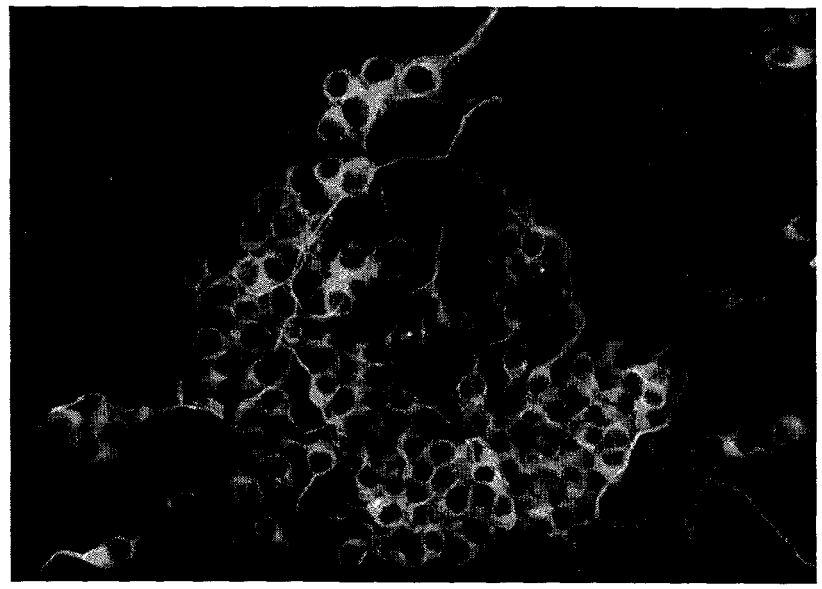
FIG. 5B

FIG. 5C
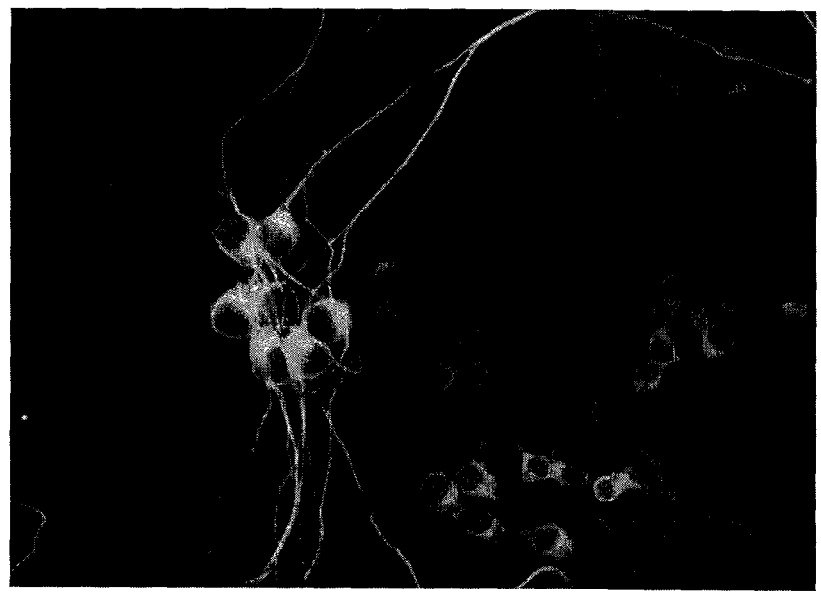
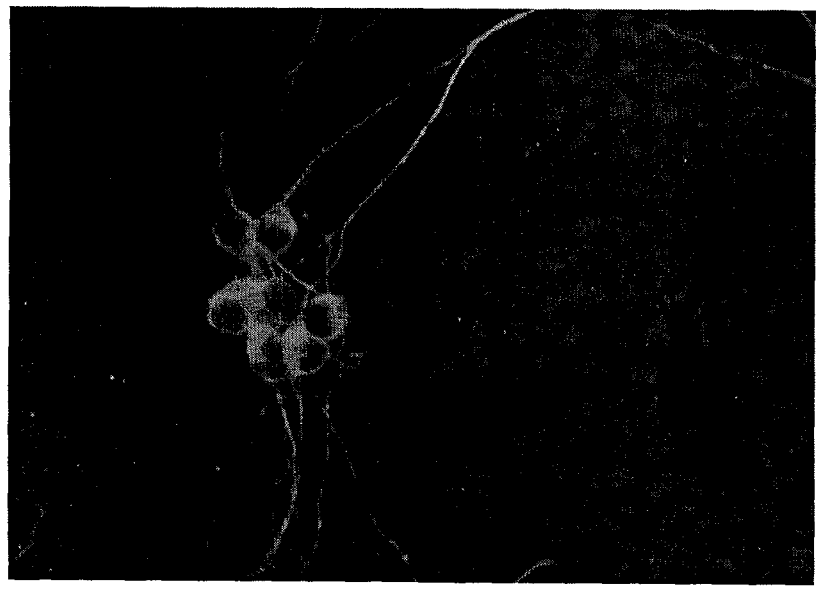
FIG. 5D

STABLE NEURAL STEM CELL LINES

This application is a continuation of co-pending U.S. patent application Ser. No. 10/047,352, filed Jan. 14, 2002, which is a continuation-in-part of U.S. patent application Ser. No. 09/053,414, filed Apr. 1, 1998 (now abandoned) and a continuation of U.S. Ser. No. 09/398,897, filed Sep. 20, 1999 (now abandoned) which claims priority to U.S. provisional application 60/101,354, filed Sep. 22, 1998; U.S. patent application Ser. No. 09/053,414 is a continuation of U.S. patent application Ser. No. 08/919,580 filed May 7, 1997 (now U.S. Pat. No. 6,040,180) and a continuation-in-part of U.S. patent application Ser. No. 08/719,450, filed Sep. 25, 1996 (now U.S. Pat. No. 5,753,506) which claims priority from U.S. provisional patent application 60/018,206, filed May 23, 1996, the entirety of each of which is hereby incorporated by reference herein.

BACKGROUND OF THE INVENTION

1. Field of the Invention

The present application discloses a systematic and efficient method for establishing stable neural stem cell lines and neuronal progenitor lines. The resulting cell lines provide robust, simple, and reproducible cultures of human and other mammalian neurons in commercially useful mass quantities while maintaining normal karyotypes and normal neuronal phenotypes.

2. Description of the Related Art

A developing fetal brain contains all of the cells germinal to the cells of an adult brain as well as all of the programs necessary to orchestrate them toward the final network of neurons. At early stages of development, the nervous system is populated by germinal cells from which all other cells, mainly neurons, astrocytes and oligodendrocytes, derive during subsequent stages of development. Clearly such germinal cells that are precursors of the normal brain development would be ideal for all gene-based and cell-based therapies if these germinal cells could be isolated, propagated and differentiated into mature cell types.

The usefulness of the isolated primary cells for both basic research and for therapeutic application depends upon the extent to which the isolated cells resemble those in the brain. Just how many different kinds of neural precursor cells there are in the developing brain is unknown. However, several distinct cell types may exist:

a unipotential precursor to neurons only ("committed neuronal progenitor" or "neuroblast"), a unipotential precursor to oligodendrocytes only ("oligodendroblast"), a unipotential precursor to astrocytes only ("astroblast"), a bipotential precursor that can become either neurons or oligodendrocytes, neurons or astrocytes, and oligodendrocytes or astrocytes, and a multipotential precursor that maintains the capacity to differentiate into any one of the three cell types.

CNS stem cells are multipotential precursor cells with the innate property to differentiate into all major cell types of the mammalian central nervous system (CNS) including neurons, astrocytes, and oligodendrocytes. The methods for isolation and differentiation of CNS stem cells and the characterization of differentiated cell types have been previously described in detail, U.S. Pat. No. 5,753,506 (Johe). Briefly, CNS stem cells are expanded in serum-free, chemically defined medium containing basic fibroblast growth factor, bFGF, as the sole mitogen. The culture condition permits nearly pure populations of CNS stem cells for a long period both as a mass culture and as a clonal culture.

The mitotic capacity of CNS stem cells, however, is finite. With the previous culture conditions, it had been difficult to expand CNS stem cells beyond about 30 celldoublings at which point a majority of the cells have lost their capacity for neuronal differentiation and further expand as glial progenitors rather than as multipotential stem cells. The mechanism for this limitation is yet unknown.

We hypothesized that mitotic CNS stem cells secrete an autocrine factor or factors which suppress the entry into cell cycle at the G1 phase of mitosis. This would effectively antagonize the mitogenic actions of bFGF and initiate the differentiation path. Thus, it is a mechanism to self-regulate the proliferation of CNS stem cells and, in vivo, to limit the generation of neurons and glia during development. Consistent with this mechanism is the observation that high cell density promptly differentiates CNS stem cells even in the presence of bFGF and regardless of the passage time.

Although the 30 cell-doublings yield $10^9$-fold expansion of cells, a method for further significant expansion of CNS stem cells would be of significant commercial value. Here, we disclose that constitutive activation of c-myc protein in CNS stem cells prevents their spontaneous differentiation at high cell density, confers resistance to glial differentiation, and increases the mitotic capacity over 60 cell-doublings. This procedure thus yields more than a $10^{18}$-fold expansion of CNS stem cells.

SUMMARY OF THE INVENTION

The present application reveals a method for producing stable cell lines of mammalian neural precursor cells in vitro. The method comprises the steps of preparing a culture of neural precursor cells in a serum-free medium; culturing the neural precursor cells in the presence of a first mitogen, where the first mitogen is selected from the group consisting of aFGF, bFGF, EGF, TGFα and combinations thereof; contacting the cells with an agent capable of being taken up by the cells and capable of expressing a c-myc gene; and further culturing the cells in a medium containing the first mitogen and a second mitogen, where the second mitogen is selected from the group consisting of aFGF, bFGF, EGF, TGFαserum and combinations thereof, with the proviso that the second mitogen is other than the first mitogen.

In a preferred embodiment of the method, the c-myc gene is fused with other DNA elements, where the other DNA elements comprise at least one element selected from the group consisting of a ligand binding domain for an estrogen receptor, an androgen receptor, a progesterone receptor, a glucocorticoid receptor, a thyroid hormone receptor, a retinoid receptor, and an ecdysone receptor.

In another preferred embodiment of the method, the medium containing the first mitogen and the second mitogen further comprises a myc-activating chemical selected from the group consisting of β-estradiol, RU38486, dexamethasone, thyroid hormones, retinoids, and ecdysone.

In a more preferred embodiment of the method, the mammalian neural precursor cells are derived from a human. In another more preferred embodiment of the method, the mammalian neural precursor cells are derived from an in vitro culture of pluripotent embryonic stem cells.

The present application also reveals a cell line produced according to this method. In a preferred embodiment of the cell line, the cells maintain a multipotential capacity to differentiate into neurons, astrocytes and oligodendrocytes. In other preferred embodiments of the cell line, the cells maintain a bipotential capacity to differentiate into neurons and astrocytes or into astrocytes and oligodendrocytes.

In more preferred embodiments of the cell line, the cells maintain a unipotential capacity to differentiate into neurons or into astrocytes.

The present application also reveals a method for producing stable clonal cell lines of mammalian neural precursor cells in vitro. The method comprises the steps of preparing a culture of neural precursor cells in a serum-free medium; culturing the neural precursor cells in the presence of a first mitogen, where the first mitogen is selected from the group consisting of aFGF, bFGF, EGF, TGFα and combinations thereof; contacting the cells with an agent capable of being taken up by the cells and capable of expressing a c-myc gene and a selectable marker; further culturing the cells in a medium containing the first mitogen and a second mitogen, where the second mitogen is selected from the group consisting of aFGF, bFGF, EGF, TGFα, serum and combinations thereof, with the proviso that the second mitogen is other than the first mitogen; and collecting c-myc treated cells and co-culturing them with feeder cells free of the selectable marker and capable of supporting survival of the c-myc treated cells in a medium containing the first mitogen and the second mitogen, with the proviso that the second mitogen is other than the first mitogen.

In a preferred embodiment of this method, the c-myc gene is fused with other DNA elements, where the other DNA elements comprise at least one element selected from the group consisting of a ligand binding domain for an estrogen receptor, an androgen receptor, a progesterone receptor, a glucocorticoid receptor, a thyroid hormone receptor, a retinoid receptor, and an ecdysone receptor.

In another preferred embodiment of this method, the medium containing the first mitogen and the second mitogen further comprises a myc-activating chemical selected from the group consisting of β-estradiol, RU38486, dexamethasone, thyroid hormones, retinoids, and ecdysone.

In a more preferred embodiment of this method the mammalian neural precursor cells are derived from a human. In another more preferred embodiment of this method, the mammalian neural precursor cells are derived from an in vitro culture of pluripotent embryonic stem cells.

The present application also reveals a cell line produced by this method. In a preferred embodiment of this cell line, the cells maintain a multipotential capacity to differentiate into neurons, astrocytes and oligodendrocytes. In other preferred embodiments of this cell line, the cells maintain a bipotential capacity to differentiate into neurons and astrocytes or into astrocytes and oligodendrocytes.

In more preferred embodiments of this cell line the cells maintain a unipotential capacity to differentiate into neurons or into astrocytes.

BRIEF DESCRIPTION OF THE DRAWINGS

FIG. 3. Stability of neuronal differentiation of MycER-modified human CNS stem cells.

A. Unmodified CNS stem cells differentiated and immunostained with anti-MAP2ab antibody;

B. Unmodified CNS stem cells differentiated and immunostained with anti-TH antibody;

C. MycER modified human cortical cells at passage 4, differentiated and immunostained with anti-MAP2ab antibody viewed at low magnification;

D. MycER modified human cortical cells at passage 4, differentiated and immunostained with anti-MAP2ab antibody viewed at high magnification;

E. MycER modified human cortical cells at passage 4, differentiated and immunostained with anti-TH antibody viewed at low magnification;

F. MycER modified human cortical cells at passage 4, differentiated and immunostained with anti-TH antibody viewed at high magnification;

G. MycER modified human cortical cells at passage 4, differentiated and immunostained with anti-GABA antibody viewed at low magnification;

H. MycER modified human cortical cells at passage 4, differentiated and immunostained with anti-GABA antibody viewed at high magnification;

I. MycER modified human cortical cells at passage 9, differentiated and immunostained with anti-MAP2ab antibody viewed at low magnification;

J. MycER modified human cortical cells at passage 9, differentiated and immunostained with anti-MAP2ab antibody viewed at high magnification;

K. MycER modified human cortical cells at passage 9, differentiated and immunostained with anti-TH antibody viewed at low magnification; and L. MycER modified human cortical cells at passage 9, differentiated and immunostained with anti-TH antibody viewed at high magnification.

Figure 4:
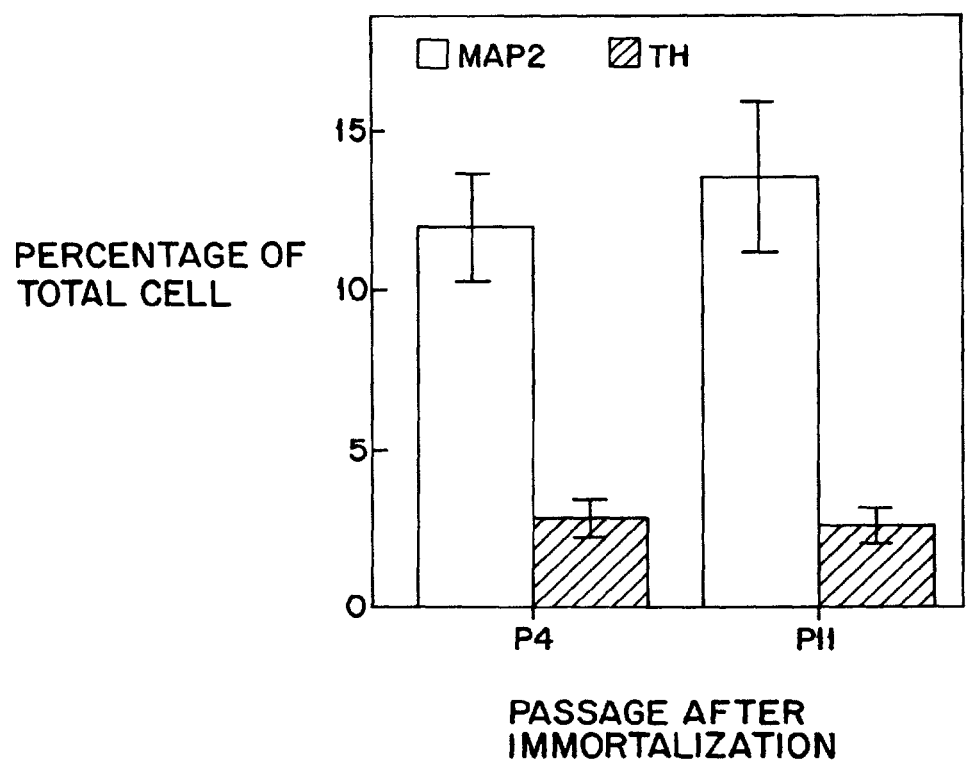

FIG. 4. Stability of neuronal differentiation. MycER-modified human cortical cell lines were differentiated at passage 4 and at passage 11. The number of neurons immunostained for MAP2ab or TH proteins were quantified and their proportions over the total cells are reported.

FIG. 5. MycER modified neuronal progenitors.

A. MycER-modified rat striatal progenitors immunostained with anti-tau antibody;

B. Morphology and arrangement of tau+/TuJ1− neuronal progenitors, immunostained with anti-tau antibody;

C. Morphology and arrangement of tau+/TuJ1+ neuronal progenitors, immunostained with anti-tau antibody; and D. Morphology and arrangement of tau+/TuJ1+ neuronal progenitors of C, immunostained with anti-TuJ1 antibody.

DETAILED DESCRIPTION OF THE PREFERRED EMBODIMENT

Neural cells in culture are highly plastic. Even a brief exposure to suboptimal culture conditions such as serum can have subtle yet significant long-term effects on the phenotype of the cells. Yet, almost all of the reported neural cultures employ serum as the primary source of mitogen. We and others have demonstrated that, in order to preserve the intrinsic differentiation potential of stem cells and other cells, it is critical to reduce the exposure of the cells to serum and that well-defined growth factors, particularly bFGF and/or epidermal growth factor, EGF, in a serum-free medium can proliferate a variety of different cell types in a single culture (Johe, U.S. Pat. No. 5,753,506; Weiss et. al., U.S. Pat. No. 5,851,832).

In the absence of a particular molecular marker for each of the cell types, isolating potentially thousands of distinct neural cell types that may exist in a single culture had not been feasible. In the previous works, we have described the methods and compositions of distinct CNS stem cell populations that give rise to a variety of different neurons in culture. Here, a reproducible and efficient method utilizing over-expression of the c-myc gene to stabilize the differentiation potentials of neural cells and to isolate stable clonal cell lines is described.

With continuous passage, CNS stem cells gradually lose their capacity to differentiate into neurons, thus becoming glial progenitors. The conditions which accelerate this process include high cell density during proliferation, poor attachment of the cells on extracellular matrix coated surface, and exposure to glia-promoting factors such as CNTF (ciliary neurotrophic factor), LIF (leukemia inhibitory factor), BMPs (bone morphogenic factors) and serum. In order to overcome this instability of neuronal differentiation capacity of CNS stem cells, we have introduced into the cells a cellular proto-oncogene, c-myc, whose activity can be regulated by the presence or absence of an extracellular molecule, 3-estradiol.

Human and rat CNS stem cells harboring the fusion gene were grown in the continuous presence of mitogens and 13-estradiol in the culture medium. Growth of the cells were significantly more robust, exhibiting faster mitotic rate, resistance to spontaneous differentiation, and much greater overall stability during the expansion. The cells showed no sign of neoplastic transformation or anomalous growth pattern or morphology. Upon withdrawal of the mitogens and β-estradiol, the cells initiated differentiation promptly and gave rise to heterogeneous morphologies characteristic of neurons and glia. Neuronal differentiation was efficient, exhibiting molecular expression patterns, localization of neurons-specific proteins, and cell morphologies and behaviors essentially indistinguishable from the parental unmodified CNS stem cells.

The neuronal population consisted of various neurotransmitter phenotypes, including the tyrosine hydroxylase-positive dopaminergic phenotype in 10-20% of the neurons. Such neuronal differentiation capacity was stable through over 60 cell doublings resulting in at least $1 \times 10^{18}$-fold increase in the number of neurons and glia derived from the stem cells. Thus, the genetic modification and the stem cell culture method described here enable the stable isolation of practically unlimited numbers of CNS stem cells from all regions of the developing mammalian brain, each CNS stem cell clone giving rise to potentially distinct neuronal subtypes in unlimited numbers. The result, then, is a library of mammalian neurons, including human, with distinct molecular/genetic repertoires representing the diverse cellular phenotypes of the mature brains.

EXAMPLES

Construction of c-Myc-Estrogen Receptor Expressing Retrovirus

Figure 1:
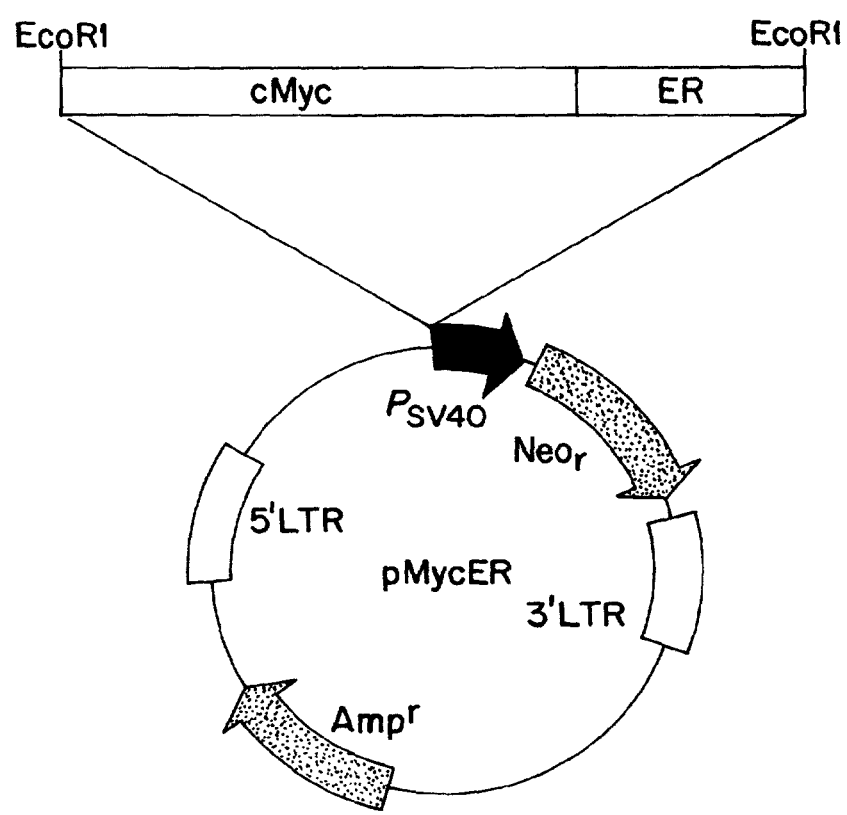
FIG. 1. Arrangement of pMycER retrovirus plasmid. A linearized EcoR1 fragment containing the human c-myc gene fused to the ligand binding domain of the human estrogen receptor gene (Eiler et al., 1989, Nature 340: 60-68) was ligated downstream of the 5'LTR of pLXSN retroviral expression plasmid (Clontech). The final construct also contains a selectable marker, the neomycin resistance gene, Neo$^r$, under the SV40 promoter, $P_{SV40}$.

A retroviral vector containing the neomycin-resistance gene under the SV40 promoter was linearized with EcoR1 and ligated with the EcoR1-fragment of the DNA encoding a fusion gene of human c-myc cDNA and human estrogen receptor cDNA (Eiler et al., 1989, Nature 340: 60-68). The fusion gene was placed under the regulation of MMLV long-terminal repeat sequence (LTR). The overall arrangement of the final retroviral vector, pMycER, is shown in FIG. 1.

Generation of a Producer Cell Line

To establish a cell line stably producing the MycER retrovirus, an amphotropic packaging cell line was transfected with pMycER plasmid. Stable clones were selected with G418 (1 mg/ml, Life Technology Inc., MD) for 4 weeks. Twenty clones were screened for high titer production against Hela cells according to standard procedure. A cell line, MycER. 10, with a retroviral titer of $10^5$ pfu/ml as measured by infection of rat striatal stem cells was selected for subsequent experiments.

Infection of Rat and Human CNS Stem Cells

Rat and human CNS stem cells were prepared according to previously reported procedure (U.S. Pat. No. 5,753,506). Passage 1 cells were plated at $0.5 \times 10^6$ cells per 100 mm plate and grown for three additional days in serum-free N2 medium plus 10 ng/ml bFGF. MycER.10 cells were grown in DMEM/10% fetal bovine serum to 50-75% confluence, subsequently rinsed three times with DMEM, and incubated for 4-16 hours in a retrovirus collection medium (IFM). IFM consisted of the standard N2 components (25 mg/L human recombinant insulin, 100 mg/L human apotransferrin, progesterone, putrescine, sodium selenite) in DMEM plus 10 ng/ml bFGF and 1 µg/ml human plasma fibronectin (hFN). IFM containing the retrovirus was clarified by two centrifugations at 1400 rpm and 3000 rpm. The supernatant was mixed with fresh N2 at a 1:1 ratio with fresh bFGF and hFN at 10 ng/ml and 1 g/ml final concentrations, respectively, and applied to the 50-75% confluent CNS stem cell culture. The infection period was typically 6 hours. Human CNS stem cells were infected for 1-3 times over a 2-3 day period to compensate for their slow mitotic rate. Subsequently, the cells were rinsed three times with $Ca^{2+}$-, $Mg^{2+}$-free Hank's balanced saline solution (HBSS), passaged, and further expanded in N2 plus 10 ng/ml bFGF.

Selection of MycER-Expressing CNS Stem Cells

The CNS stem cells with stable incorporation of MycER retrovirus were passaged 1-2 days after the infection, replated at $0.5 \times 10^6$ cells per 100 mm plate, and selected from 2 days after the infection with 0.1-0.2 mg/ml G418, pH 7.4. The complete, optimal growth medium (IGM) was composed of DMEM/F12 (1:1), 25 mg/L human recombinant insulin, 100 mg/L human apotransferrin, progesterone, putrescine, sodium selenite, 10 ng/ml bFGF, 0.2 µM β-estradiol, 0.1 mg/ml G418, and 10 ng/ml EGF or 1% fetal bovine serum. Fresh bFGF (10 ng/ml, final concentration) was added daily and medium was changed once every two days. The cells were passaged at approximately 50-75% confluence by rinsing three times with HBSS and trypsin (1×) treatment. Trypsin activity was stopped by adding soybean trypsin inhibitor (1 mg/ml final concentration).

Isolation of Clones

At the end of the G418 treatment for 14 days, the cells were passaged and replated approximately 200-1000 cells per 100 mm plate. Within 24 hours post plating, well-isolated single cells were marked with 3 mm circles on the bottom of the culture plate. Sometimes, the complete culture medium was mixed with an equal volume of the medium conditioned by the same cells at high cell density to enhance cell survival. Marked clones were picked with the aid of cloning rings and by trypsin treatment. Individual clones were expanded as the mass culture and stored frozen.

Almost all of the clones generated this way eventually assumed glial morphology and failed to differentiate into neurons, even though the culture conditions are identical as those for the high density culture. Thus, it became apparent that the MycERmodified cells in the presence of serum required a relatively high cell density in order to maintain their native differentiation potentials and survive. Thus, the cell density was maintained in the range of $0.5 \times 10^6$ to $1.0 \times 10^6$ cells per 100 mm plate by supplementing the clonal density of MycER-expressing cells with unmodified primary stem cells. By maintaining antibiotic selection over 5-8 days with 0.1 mg/ml G418, the feeder cell population was gradually killed while permitting local cell density of G418-resistant MycER cells to gradually rise so as to sustain their optimal growth. The antibiotic selection was maintained throughout subsequent expansion to ensure all remaining cells were MycER-modified cells.

In addition to neural stem cells, immature glial cells and mature astrocytes of both human and rat origin were effective. Fibroblasts were also useful, but more difficult to manage because their rapid proliferation rate and their high tolerance to G418. Neurons may also be useful, but their post-mitotic nature rendered them much more resistant to G418. Non-mitotic fibroblasts and other non-neural cells which had been gamma-irradiated or treated with mitotic inhibitors such as arabinoside C or mitomycin may also be effective in supporting the c-myc-modified neural cells.

Differentiation and Characterization of the Mitotically Enhanced CNS Stem Cells

CNS stem cells stably expressing MycER were differentiated by plating the cells at 100,000 cell/cm² or higher cell density and replacing the growth medium with N2 without bFGF, without serum, and without β-estradiol. Typically, the cells were allowed to differentiate for 6-30 days before immunohistochemical analysis.

Results

1. Search for Additional Factors Enhancing Mitotic Capacity of CNS Stem Cells

The doubling time for human CNS stem cells in N2 medium with bFGF as the sole mitogen is approximately 60 hours which is markedly slower than 24 hours for rat CNS stem cells under the identical culture conditions. This may be due to a species difference in certain cell-autonomous properties of the cells such as a difference in DNA replication rate or in other mitotic phases, G1 or G2, of the cell cycle. We investigated other factors to accelerate the mitotic rate of human CNS stem cells.

Many purified recombinant human growth factors were tested for the ability to enhance the mitogenic activity of bFGF. The mitotic rate of human CNS stem cells was assessed by measuring the proportion of the cells which have incorporated the mitotic label, bromodeoxyuridine (BrdU), during a 24-hour period. Each growth factor was supplied daily to the culture in addition to bFGF. Only the combination of bFGF+EGF and bFGF+TGFα (transforming growth factor-alpha) accelerated beyond the bFGF-induced mitotic rate of the human CNS stem cells. In both conditions, the doubling time of the cells increased 1.5 times to 40 hours over bFGF alone. Combination of bFGF and fetal bovine serum at 1% or at 10% also accelerated the BrdU-incorporation rate of bFGF-induced mitotic rate of CNS stem cells to a similar rate.

2. Resistance of CNS Stem Cells Against Spontaneous Differentiation

Although EGF, TGFα, % FBS, or 10% FBS plus bFGF increased the mitotic rate of human CNS stem cells, even under these conditions, CNS stem cells were susceptible to spontaneous differentiation at near-confluent cell density and also prone to drift toward glial progenitor states with multiple passages. In order to provide enhanced mitotic capacity and greater stability to the neuronal differentiation capacity of CNS stem cells, we constructed a retroviral vector expressing a fusion protein of human c-myc and human estrogen receptor genes under the MMLV long terminal repeat (FIG. 1).

Dividing mammalian CNS stem cells were infected by the amphotropic retrovirus with high efficiency and the resulting cells selected by their resistance to G418 treatment. The transcriptional activity of c-myc in the fusion protein (MycER) was regulated by the presence or absence of the estrogen receptor ligand, β-estradiol, in the culture medium. Moreover, the promoter activity of the long terminal repeat is shut down during CNS stem cell differentiation into neurons, effectively eliminating MycER transcript. Combination of the withdrawal of mitogens, absence of β-estradiol, and limited transcription activity of LTR resulted in an efficient constitutive differentiation of CNS stem cells in a manner indistinguishable from the unmodified parental cells.

CNS stem cells from various regions and developmental stages of human fetal brains were infected at passage1 with the MycER-expressing retrovirus. Infected cells were selected by G418 resistance and expanded in N2B medium (N2 without phenol red) containing bFGF, 10 ng/ml EGF or 1% FBS, and β-estradiol. Expression of MycER itself did not cause a significant change in the mitotic rate of the cells; however, the addition of EGF and/or FBS significantly increased the mitotic rate and enhanced the overall stability of the culture. The cells proliferated robustly, maintained stable morphologies over many successive passages, and sustained their multipotentiality without spontaneous differentiation even at nearly confluent cell density. Upon replacement of the growth medium with N2B without any mitogen and without β-estradiol, the stem cells promptly differentiated to give rise to neurons, astrocytes and oligodendrocytes.

3. Expansion Capacity of the Mitotically Enhanced CNS Stem Cell Lines

Figure 2:
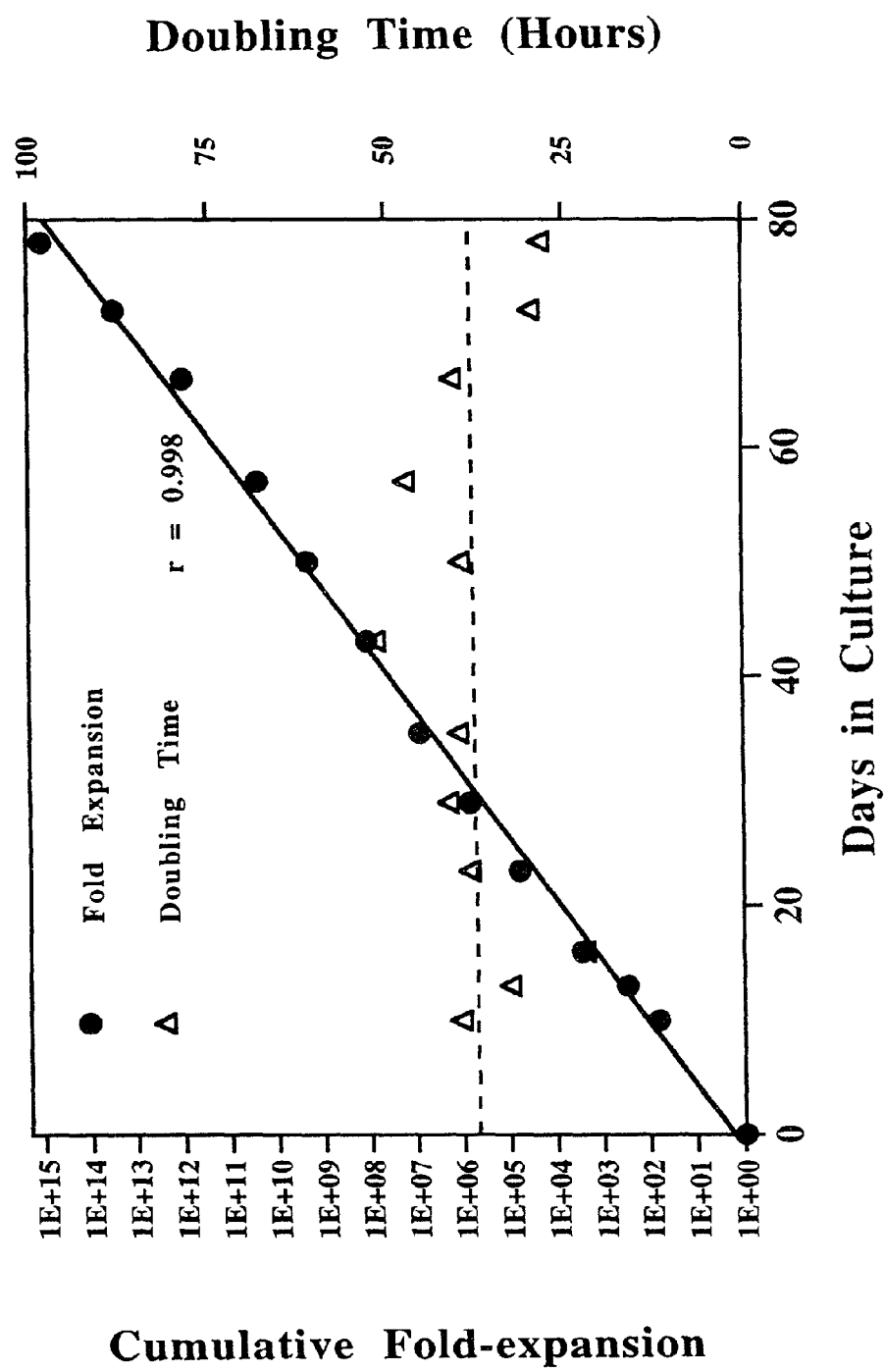
FIG. 2. Growth capacity of MycER-modified human CNS stem cells. In order to measure the growth rate and capacity, a MycER-modified human CNS stem cell line pool (HK18.2) derived from 18-week old human fetal cortical tissue was continuously expanded in culture for approximately 80 days. At each passage (solid circle), the cells were harvested, counted, and a fraction replated into new plates. This process was repeated for 12 passages. By dividing the increased cell number from the initial seeding density to the time of harvest by the duration of the culture per passage, an approximate doubling time was estimated (open triangle). The dotted line across the graph represents the averaged doubling time for the entire culture period. Cumulative expansion of the cells was calculated by multiplying the multiples of increased cell number at each passage and expressed as "Cumulative Fold-Expansion" over the initial cell number at day 0. The initial starting cell number at day 0 was $5.0 \times 10^6$ cells.

To ascertain the extent of the mitotic and differentiative capacity of the MycER-modified human CNS stem cell line, the cells were expanded continuously for 80 days in culture and through 12 passages since the infection event. During this period, the cell yield at each passage was measured to quantify the actual arithmetic increase in cell number and to determine the stability of the mitotic rate over time (FIG. 2). Overall, the cells went through approximately 54 doublings which resulted in $10^{15}$-fold increase in the cell number. The doubling time of the cells was remarkably constant at about 40 hours per mitosis, which is unchanged from that of the parental primary human CNS stem cells (FIG. 2).

The same human CNS stem cell preparation was also subjected to MycER-retrovirus infection and grown in bFGF alone or in bFGF and EGF. In bFGF alone as the mitogen, the MycER-expressing CNS stem cells exhibited enhanced mitotic capacity over the unmodified cells, but yet showed far less proliferative capacity than in bFGF+1% FBS. As with the unmodified parent cells, the MycER cells also retained a 60 hour doubling time in bFGF alone. On the other hand, in bFGF+EGF, the MycER expressing stem cells displayed increased mitotic rate, increased mitotic capacity, increased stability of neuronal differentiation capacity, and were resistant to spontaneous differentiation quite similar to the bFGF+1% FBS condition. In the absence of MycER expression, the same three conditions yielded a similar pattern of growth, but with less stability. Significantly, the bFGF+1% FBS condition, although resulting in more efficient cell growth, inevitably led to the loss of the neuronal differentiation capacity. This demonstrates that the constitutive c-myc function in these cells is subtle: It provides more stable multipotentiality and enhanced mitotic capacity but not an overt mitogen-independence or transformation.

These effects of the constitutively active c-myc could also be extended to CNS stem cells from all regions of rat and human fetal brains.

4. Neuronal Differentiation of MycER-Enhanced CNS Stem Cells

The MycER-enhanced CNS stem cells were differentiated by withdrawing the mitogens and β-estradiol from the medium and without addition of exogenous factors. Divergence of neuronal and glial morphologies began to occur within two days. By the third day, neuronal morphologies were clearly distinguishable. The neurons continued to mature into fully functional neurons over the next 3-5 weeks.

The differentiated cultures from the MycER-enhanced human CNS stem cells at different passages were analyzed by immunohistochemistry with a variety of different cell-type specific antibodies. At 10 days of differentiation, approximately 50% of the total cells expressed MAP2c, tau, and tubulin llb proteins, all relatively early markers of neuronal differentiation. Approximately 20-30% of the total cells expressed the mature markers of neurons, MAP2a and MAP2b proteins. Various neurofilament antibodies revealed a similar proportion of neurons. Of the neurons, approximately 70% were GABA-positive. A similar proportion of neurons was also calretinin-positive. Approximately 10-20% of the neurons expressed tyrosine hydroxylase (TH), the key biosynthetic enzyme for dopamine. All of the immunopositive neurons were of typical neuronal morphologies and did not co-express the glial marker, GFAP. Thus, MycERenhanced cell lines differentiate to generate a high proportion of neurons exhibiting various neurotransmitter phenotypes.

The proportions and neurotransmitter phenotypes of the neurons were stable through many successive passages (FIG. 3A-L). Throughout 54 stem cell doublings, there was no degradation of the neuronal differentiation capacity in both the proportion of neurons as well as in the various neurotransmitter phenotypes generated.

5. Region-Specific Stem Cell Lines

The serum-free culture condition used for isolation of neural stem cells permitted stable inheritance of regional identities and their related neurotransmitter phenotypes through multiple cell divisions. This implies that the stem cells in the culture, although they are uniform in their ability to differentiate into neurons and glia, may be extremely diverse. Thus, if each stem cell in the beginning of the culture could be immortalized in its native state and if this method was efficient to sample thousands of stem cells in a single dish, then the diverse neuronal phenotypes might be permanently "captured" in the form of cell lines.

The genetic modification of neural stem cells with c-myc resulted in robust, highly reproducible and in a stable cell culture system. The modification process itself is quite efficient, yielding 5,000 to 50,000 independent clones per retrovirus infection over a two day process. This could be easily scaled up by increasing the retrovirus particles or increasing the number of target cell density, if needed.

In order to ascertain whether over-expression of c-myc has an impact on differentiation capacity of neurotransmitter phenotypes, stem cells from many different regions of the fetal brains of rat and human were modified by the MycER retrovirus. These regions included cortex, septum, hippocampus, midbrain, hindbrain, striatum, and spinal cord. Multiple examples of cortical, midbrain, and spinal cord cultures from several different gestational ages were examined to assess the reproducibility of the method. In all cases, the resulting pools of independent clones generated highly reproducible ratios of neurons to glia. As expected, morphologies, antigenic profiles of the neurons, and their relative ratios were also distinct from cell lines of one region versus another.

Thus, when several pools of cell lines from midbrain tissues of 8 week human fetuses were examined, approximately 0.1% of total cells were consistently TH-positive dopaminergic neurons, which is also the proportion found in the unmodified stem cell cultures. Clonal analysis revealed that the TH expression was clonally restricted. That is, a majority of the clones did not contain neurons expressing TH. Of those that did, the proportion was variable from one clone to the next. Several pools of cell lines from cortical tissues of 17-20 week old human fetuses were also examined. Interestingly, all of the cortical lines gave rise to significantly increased TH-positive neurons compared to the unmodified stem cells. The proportion of TH-positive neurons was 2-4% of the total cells. Subsequently clonal analysis revealed a similar pattern in the distribution of the TH-positive neurons. The majority had none, while those that generate TH were present in variable proportions. This pattern had also been observed with clones of unmodified stem cells from several different regions and with several different antigenic markers.

Cell lines from spinal cord of 6-10 week old human fetuses were also established. The pattern of neuronal differentiation was the same as from other regions, although their stem cell morphology and growth characteristics were distinct.

Thus, the genetic modification of neural stem cells with c-myc does not alter their intrinsic differentiation capacities. In all of the cell lines through extensive continues culture periods, no evidence of tumor formation or other abnormal transformation was noted. Upon karyotype analysis of one pool of human cortical cell lines at passage 14, a normal diploid chromosome pattern with no aberrant rearrangement was observed. Thus, regulation of mitotic capacity by c-myc, which is a cellular gene normally present in every eukaryotic cell and a well-known key regulator of cell cycle machinery, is not oncogenic and provides significant advantages over other methods using viral oncogenes such as v-myc or SV40 large T antigen.

6. Other Cell Types

The genetic modification with c-myc can be made at any time during the culture period. Since the expression of c-myc itself is not mitogenic, i.e., non-transforming, a culture condition which promotes the proliferation of a particular neural precursor population is a prerequisite. Purified growth factors such as aFGF (acidic fibroblast growth factor), bFGF, EFG and TGFα can proliferate a variety of different neural cell types. Although most of the descriptions above were on multipotent CNS stem cells as one predominant population, several different cell types were observed during clonal analysis.

One significant population was a population of bipotential progenitor clones which, upon differentiation, gave rise to neurons and astrocytes with apparent absence of oligodendrocytes. These bipotential progenitors were quite similar to the multipotential stem cells in their morphology during growth. The differentiation pattern was also similar giving rise to about 50% neurons and 50% astrocytes. Thus, key defining difference between the two populations is the absence of oligodendrocytes in differentiated cultures.

A second cell population arising from c-myc modification of primary neural cultures was a population of unipotential neuronal progenitor clones which consisted only of neurons. These neuronal progenitor clones were of smaller clone size and assumed distinct, immature neuronal morphologies during proliferation and expressed tau proteins and/or beta-tubulin III Examples are provided in FIG. 5. Two distinct cell types were observed (FIG. 5A). One type was small-bodied cells with very short single process stemming out from the cell body, which grew in tight clusters. These cells were immunoreactive with anti-tau antibody but not with anti-tubulin IIIb antibody while dividing (FIG. 5B). The other type of cells were cells with distinctively elongated neurites without extensive branching, which grew in a smaller, more scattered pattern suggesting higher migratory capacity. In contrast to the first type, they were also immunoreactive with both anti-tau antibody and with anti-tubulin lllb antibody (FIG. 5C and 5D, respectively). Often times, the second cell types were-found near or intermixed with the first cell type suggesting that they are two stages of a single continuous lineage-committed neuronal progenitors, with tau+/TuJ1+ state being the more mature state.

A third cell population arising from c-myc-modified neural cell culture was a population of clones consisting of glia only. Most of these clones were astrocytic with little or no oligodendrocytes.

Those results indicate that many neural precursor lineages respond similarly to the over-expression of c-myc. In addition to primary neural cultures prepared from nervous system tissues of mammals, recent advances in embryonic stem cell cultures indicate that various neural precursors form in vitro during differentiation of totipotential or pluripotent embryonic stem cells and cell lines maintained in culture for long term (Renoncourt et al., Mech. Dev. (1998) 78, 185; Svendsen et al., Trends Neurosci. (1999) 22, 357; Brustle et al., Science (1999) 285, 754). These cultures can generate nestin-positive neural precursor cells which can then be transferred to serum-free medium and subsequently expanded with bFGF and/or EGF for short term. Long-term, mass expansion has not been feasible since the initial neural precursor formation is inefficient. However, by utilizing the genetic modification method with the c-myc gene described here, those transient neural precursors may be turned into stable cell lines.

Neural precursors including multipotential neural stem cells can be isolated from adult brains and can be cultured in serum-free conditions. However, this process is inefficient, resulting in only a small number of proliferative cells. However, with the transfer of c-myc gene as described here, one can establish stable cell lines from such small number of cells obtained from neural tissue biopsies.

c-myc is involved in many different cellular processes such as apoptosis in addition to cell cycle regulation. c-myc has been used previously to transform cells of non-neural origins. However, these previous studies were done with already stable cell lines such as 3T3 fibroblast cell lines and to produce neoplastic state of the cell lines, which had been selected based on spontaneous chromosomal aberrations which conferred mitogen-independence. Other studies tried to use an immortalization process to turn post-mitotic neurons to re-enter the cell cycle.

CNS stem cells are already mitotic and the mitogenic culture conditions for a long-term expansion of up to 30 cell doublings has already been established. Thus, our objective has been to increase the expansion capacity well beyond the 30 cell doublings at least up to the beginning of senescence which is thought to occur between 60 and 80 cell cycles. Sixty cell doublings represent an $1\times10^{18}$-fold increase in cell number which is large enough for screening one million chemical libraries, each consisting of 500,000 compounds or large enough to provide cell therapies for 50 billion Parkinson's patients. The key concept has been to find a "gentle" modification of the cells so as not to disrupt their intrinsic neuronal differentiation capacity while providing an enhanced growth capacity under the culture conditions established for primary CNS stem cells.

Increasing the concentration of active c-myc protein leads to the generation of stable human CNS stem cell lines. This effect occurs not by overtly deregulating mitotic and differentiation parameters of the cell cycle but by providing resistance to autocrine and paracrine factors that induce restriction of multipotentiality toward a glial progenitor state. The consequence is not an oncogenic transformation of the cells but rather a stabilization of the cell growth. Thus, endogenous signals which trigger the differentiation, such as those present at confluent cell density, are still effective. The cell division is still dependent upon the supply of proper exogenous mitogens such as bFGF and/or EGF and/or serum. Differentiation of the stem cell lines to mature functional neurons is as efficient at the end of the 60-cell doublings as in the unmodified primary cells. A variety of neurotransmitter phenotypes and their relative proportions are maintained throughout the expansion.

The c-myc activity in these examples was controlled by constructing a chimeric protein of c-myc fused to a fragment of estrogen receptor protein (Eiler et. al., Nature (1988) 340, 60). The intended role of the estrogen is to provide a control over the amount of functionally active c-myc induced in the cell. The estrogen receptor portion of the chimeric protein is activated when it binds with a cell-permeable agonist or antagonist such as estradiol or tamoxifen.

Most members of the nuclear receptor superfamily act similarly in that cell-permeable ligands diffuse through the plasma bilayer and bind to their receptor which is then transported to the nucleus as a complex and induces a variety of transcription related events. The ligand binding domain of these nuclear receptor proteins and their ligands can substitute for the estrogen receptor and β-estradiol in order to regulate functions of the fused c-myc protein moiety. Examples of such nuclear receptors are glucocorticoid receptor, progesterone receptor, androgen receptors, vitamin D receptor, thyroid hormone receptors, retinoic acid receptors, and ecdysone receptor. Each of these receptors can be activated intracellularly by adding to the culture medium its appropriate ligands. Examples of the ligands are steroid hormones such as glucocorticoid or dexamethasone, thyroid hormones, retinoids such as retinoic acids, vitamin D, and the insect molting hormone, ecdysone, as well as their synthetic analogs designed to act on the respective receptors. All of these compounds are small, hydrophobic molecules which can traverse the cell membrane once supplied extracellularly.

Some receptor-ligand systems are better suited than others for the purpose of regulating the over-expressed c-myc. For instance, for the purpose of transplanting cmyc-modified cells into tissues as a treatment of a disease, it would be desirable that the c-myc-receptor chimeric protein should not respond to endogenous physiological ligands. The c-myc-estrogen receptor described here has the disadvantage that potentially high level of estrogen present in female patients may have unexpected effects on the cells. In another instance, the ligands used to control the c-myc activity in culture may have their own unrelated effects on endogenous receptors. Thus, an ideal receptor-ligand system is one in which the receptor moiety of the fusion protein does not recognize the endogenous ligand and in which the ligand is a synthetic compound which has no adverse effect on the cells. One such potential system is human progesterone receptor and its antagonist ligand, RU38486. It has been established that the ligand binding fragment of the human progesterone receptor does not respond to the endogenous ligand, progesterone but is sensitively activated by a synthetic analog of progesterone, RU38486, while RU38486 does not activate the endogenous full-length progesterone receptor (Wang et al., Proc Natl. Acad. Sci. USA (1994) 91, 8180).

Thus, one enhanced c-myc expression system to produce stable cell lines would be to construct a plasmid in which the human c-myc gene is fused to the ligand binding domain of the human progesterone receptor with the C-terminal deletion of 12 amino acids, to cut out the fused DNA (c-mycPR), ligate to the retroviral plasmid, pLXSN, at downstream of 5' LTR, and to generate the intact retrovirus expressing the chimeric protein, c-myc-progesterone receptor (MycPR).

The commercial utilities of the mitotically enhanced CNS stem cells are: cell transplantation of the TH-positive dopaminergic neurons to treat Parkinson's disease; substrate for screening potential pharmacological compounds; a reproducible source of gene and protein levels of the cells influenced by a specific agent or protocol designed to represent/mimic a disease process; a reproducible source of novel genes and proteins; a reproducible source of neurons and glia for engineering of three dimensional tissues and neural prosthesis; a delivery vehicle of potentially therapeutic large molecule compounds such as NGF to treat Alzheimer's disease; and the starting population to further derive in vitro various committed neuronal progenitor populations such as proliferative TH-expressing neuronal cells.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims. Thus, it is to be understood that variations in the present invention can be made without departing from the novel aspects of this invention as defined in the claims. All patents and articles cited herein are hereby incorporated by reference in their entirety and relied upon.

What is claimed is:

1. A method for producing a stable cell line of human neural precursor cells in vitro, comprising the steps of:
   a) preparing a culture of neural precursor cells in a serum-free medium;
   b) culturing the neural precursor cells in the presence of a first mitogen, wherein said first mitogen is selected from the group consisting of aFGF, bFGF, EGF, TGFα and combinations thereof;
   c) introducing into the neural precursor cells a recombinant DNA construct comprising a receptor ligand-regulated c-myc gene, wherein the c-myc gene is fused with DNA encoding a ligand-binding domain of a nuclear receptor;
   d) contacting the neural precursor cells with an agent that binds the ligand-binding domain of the nuclear receptor, wherein the agent comprises a myc-activating chemical selected from the group consisting of β-estradiol, RU38486, dexamethasone, thyroid hormones, retinoids, and ecdysone;
   e) further culturing the neural precursor cells in a medium containing the first mitogen and a second mitogen to produce a stable cell line of neural precursor cells, wherein said second mitogen is selected from the group consisting of aFGF, bFGF, EGF, TGFα, serum and combinations thereof, with the proviso that the second mitogen is other than the first mitogen, and
   f) expanding the neural precursor cells of the stable cell line beyond thirty cell doublings in the medium containing the first mitogen and the second mitogen,
   wherein the expanded neural precursor cells of the stable cell line of neural precursor cells are capable of differentiating into neurons, astrocytes, and oligodendrocytes after removal of the first and second mitogen from the medium.

2. The method of claim 1, wherein the c-myc gene is fused with a DNA sequence coding for a ligand-binding domain of a nuclear receptor selected from the group consisting of a ligand binding domain for an estrogen receptor, an androgen receptor, a progesterone receptor, a glucocorticoid receptor, a thyroid hormone receptor, a retinoid receptor, and an ecdysone receptor.

3. The method of claim 1, wherein the human neural precursor cells are derived from an in vitro culture of pluripotent embryonic stem cells.

4. A cell line produced according to the method of claim 1.

5. The cell line of claim 4, wherein the neural precursor cells of the produced stable cell line maintain a multipotential capacity beyond thirty cell doublings to differentiate into neurons, astrocytes and oligodendrocytes.

6. The cell line of claim 4, wherein the neural precursor cells of the produced stable cell line maintain a bipotential capacity beyond thirty cell doublings to differentiate into neurons and astrocytes.

7. The cell line of claim 4, wherein the neural precursor cells of the produced stable cell line maintain a bipotential capacity beyond thirty cell doublings to differentiate into astrocytes and oligodendrocytes.

8. The cell line of claim 4, wherein the neural precursor cells of the produced stable cell line maintain a capacity beyond thirty cell doublings to differentiate into neurons.

9. The cell line of claim 4, wherein the neural precursor cells of the produced stable cell line maintain a capacity beyond thirty cell doublings to differentiate into astrocytes.

10. A method for producing a stable human neural precursor cells clone in vitro, comprising the steps of:
    a) preparing a culture of neural precursor cells in a serum-free medium;
    b) culturing the neural precursor cells in the presence of a first mitogen, wherein said first mitogen is selected from the group consisting of aFGF, bFGF, EGF, TGFα and combinations thereof;
    c) introducing into the neural precursor cells a recombinant DNA construct comprising a retroviral vector containing the neomycin-resistance gene and a fusion gene of human c-myc cDNA and human estrogen receptor cDNA;
    d) further culturing the neural precursor cells in a medium containing the first mitogen and a second mitogen, wherein said second mitogen is selected from the group consisting of aFGF, bFGF, EGF, TGFα, serum and combinations thereof, with the proviso that the second mitogen is other than the first mitogen, wherein the medium includes G418 to select for the neural precursor cells containing the recombinant DNA construct, wherein the medium includes β-estradiol;

e) plating the neural precursor cells obtained from step d) at a cell density of $0.5\times10^6$ to $1.0\times10^6$ cells per 100 mm plate by supplementing the neural precursor cells with unmodified primary cells in the continued presence of G418 in a medium containing the first mitogen and the second mitogen, and f) expanding the neural precursor cells of the stable cell line beyond thirty cell doublings in the continued presence of G418 in the medium containing the first mitogen and the second mitogen, and g) isolating a stable neural precursor clone from the plated neural precursor cells.

11. The method of claim 10, wherein the human neural precursor cells are derived from an in vitro culture of pluripotent embryonic stem cells.

12. A cell line produced according to the method of claim 10.

13. The cell line of claim 12, wherein the neural precursor cells of the produced stable cell line maintain a multipotential capacity beyond thirty cell doublings to differentiate into neurons, astrocytes and oligodendrocytes.

14. The cell line of claim 12, wherein the neural precursor cells of the produced stable cell line maintain a bipotential capacity beyond thirty cell doublings to differentiate into neurons and astrocytes.

15. The cell line of claim 12, wherein the neural precursor cells of the produced stable cell line maintain a bipotential capacity beyond thirty cell doublings to differentiate into astrocytes and oligodendrocytes.

16. The cell line of claim 12, wherein the neural precursor cells of the produced stable cell line maintain a capacity beyond thirty cell doublings to differentiate into neurons.

17. The cell line of claim 12, wherein the neural precursor cells of the produced stable cell line maintain a capacity beyond thirty cell doublings to differentiate into astrocytes.

18. The cell line of claim 12, wherein the neural precursor cells of the produced stable cell line maintain a capacity beyond thirty cell doublings to differentiate into oligodendrocytes.

19. The cell line of claim 4, wherein the neural precursor cells of the produced stable cell line maintain a capacity beyond thirty cell doublings to differentiate into oligodendrocytes.

* * * * *